US007192395B1

(12) United States Patent
Qu et al.

(10) Patent No.: US 7,192,395 B1
(45) Date of Patent: Mar. 20, 2007

(54) MODIFICATION OF POLYMER SURFACES AS RADIOISOTOPE CARRIERS

(75) Inventors: Xin Qu, New York, NY (US); Judah Z. Weinberger, Teaneck, NJ (US)

(73) Assignee: The Trustees of Columbia University in the City of New York, New York, NY (US)

( * ) Notice: Subject to any disclaimer, the term of this patent is extended or adjusted under 35 U.S.C. 154(b) by 1225 days.

(21) Appl. No.: 09/657,701

(22) Filed: Sep. 8, 2000

(51) Int. Cl.
*A61N 5/00* (2006.01)
(52) U.S. Cl. .................. 600/1; 404/1.37; 404/1.65
(58) Field of Classification Search ............... 600/1–8; 424/1.33, 1.29, 1.25, 1.37, 1.65, 1.73; 514/55; 536/20; 252/625, 634–635; 427/5
See application file for complete search history.

(56) References Cited

U.S. PATENT DOCUMENTS 5,713,828 A * 2/1998 Coniglione .................... 600/7
5,762,903 A    6/1998 Park et al.

FOREIGN PATENT DOCUMENTS

WO       9917812       4/1999

OTHER PUBLICATIONS

Gruentzig AR, King SB, Schlumpf M, et al. Long-term follow-up after percutaneous transluminal coronary angioplasty. N Engl J Med 1987; 316:1127-32 (Exhibit 4).
Nobuyoshi M. Kimura T, Nosaka H, et al. Restenosis after successful percutaneous transluminal coronary angioplasty: serial angiographic follow-up of 229 patients. J Am Coll Cardiol 1988;12:616-23 (Exhibit 5).
Urban P, Buller N, Fox K, et al. Lack of effect of warfarin on the restenosis rate or on clinical outcome after ballon coronary angioplasty. Br Heart J 1988;60: 485-8 (Exhibit 6).
Wiedermann JG, Marboe C, Amols H, Schwartz A, Weinberger J. Intracoronary irradiation markedly reduces restenosis after balloon angioplasty in a porcine model. JACC 1994;23(6) :1491-8 (Exhibit 7).
Wiedermann JG, Marboe C, Amols H, Schwartz A, Weinberger J. Intracoronary irradiation markedly reduces neointimal proliferation after balloon angioplasty in swine: persistent benefit at 6-month follow-up. JACC 1994;25(6) :1451-6 (Exhibit 8).
Mazur W, Ali MN, Khan MM, Dabaghi SF, DeFelice CA, Paradis JP, Butler EBA, Wright E, Fajardo LFB, French A and Raizner AE. High dose rate intracoronary radiation for inhibition of neointimal formation in the stented and balloon-injured porcine models of restenosis: Angiographic, morphometric, and histopathologic analysis. Int J Rad Onc Biol Phys 1996; 36(4):777-788 (Exhibit 9).
Waksman R, Robinson KA, Crocker IR, Gravanis MB, Cipolla GD, and King SR. Endovascular low-dose irradiation inhibits neointima formation after coronary artery balloon injury inswine: A possible role for radiation therapy in restenosis prevention. Circulation 1995;91(5) :1533-9 (Exhibit 10).

Verin V, Popowski Y, Urban P, et al. Intra-arterial beta irradiation prevents neointimal hyperplasia in a hypercholesterolemic rabbit restenosis model. Circulation 1995;92:2284-90 (Exhibit 11).
Condado JA, Waksman R, Gurdiel O, et al. Long-term angiographic and clinical outcome after percutaneous transluminal coronary angioplasty and intracoronary radiation therapy in humans. Circulation 1997;96:727-32 (Exhibit 12).
Teirstein PS, Massullo V, Jani S, et al. Catheter-based radiotherapy to inhibit stenosis after coronary stenting. N Engl J Med 1997;336:1697-703 (Exhibit 13).
Verin V, Urban P, Popowski Y, et al. Feasibility of intracoronary B-irradiation to reduce restenosis after balloon angioplasty, a clinical pilot study. Circulation 1997;95:1138-44 (Exhibit 14).
Weinberger J. Intracoronary radiation using radioisotope solution filled balloons. Herz 1998;23:366-72 (Exhibit 15).
Guibal E. Dambies L, Milot C, Roussy J. Influence of polymer structural parameters and experimental conditions on metal anion sorption by chitosan. Polym Intern 1999:48(8) :671-80 (Exhibit 16).
Qu X, Wirsen A, Albertsson AC. Structural change and swelling mechanism of ph-sensitive hydrogels based on chitosan and D, L-lactic acid. J Appl Polym Sci 1999;74(13) :3186-92 (Exhibit 18).
Qu X, Wirsen A, Albertsson AC. Synthesis and characterization of pH-sensitive hydrogels based on chitosan and D, L-lactic acid. J Appl Polym Sci 1997;74(13) :3193-02 (Exhibit 19).
Pioletti DP, Takei H, Lin T, et al. The effect of calcium phosphate cement particles on osteoblast functions. Biomaterials 2000;21 : 1103-14 (Exhibit 20).
Varma HK, Yokogawa Y, Espinosa FF, et al. Porous calcium phosphate coating over phosphorylated chitosan film by a biomimetic method. Biomaterials 1999;20: 879-84 (Exhibit 21).
Zamora PO, Osakis, Som P, Ferretti JA, Choi JS, Hu C, Tsang R, Kuan HM, Singletary S, Stern R A, Oster ZH, Radiolabeling Brachytherapy Sources with Re-188 through Chelating Microfilms: Stents, Journal of Biomedical Materials Research, vol. 53, No. 4 pp. 244-251 (May 11, 2000) (Exhibit 22).

(Continued)

*Primary Examiner*—John P. Lacyk
(74) *Attorney, Agent, or Firm*—John P. White; Cooper & Dunham LLP

(57) ABSTRACT

A radioactive source is made by forming a polymer layer substantially free of inorganic polymers on a substrate material, and exposing the polymer layer to a radioactive isotope. The source is useful for inhibition of restenosis in coronary arteries after balloon angioplasty or stent implantation. In particular, a radioactive source of $^{32}P$, $^{90}Y$, or $^{144}Ce$ is deposited on a poly(ethylene terephtalate) (PET) substrate. The polymer substrate was first coated with pH-sensitive hydrogel and then adsorbed various amount of phosphoric acid (PA) in aqueous solutions. The substrate was immersed in $^{32}P$, $^{90}YCl_3$ or $^{144}CeCl_3$ solutions, and then $^{32}P$, $^{90}Y$ or $^{144}Ce$ was deposited on the surface as $^{32}PPO_4$, $^{90}YPO_4$ or $^{144}Ce\,PO_4$. Two different polyurethanes were used to encapsulate and seal the deposited isotopes on the surface to minimize the leakage of the isotope.

30 Claims, 22 Drawing Sheets

OTHER PUBLICATIONS

Muller DWM, Ellis SG, Topol EJ. Colchicine and antineoplastic therapy for prevention of restenosis after percutaneous coronary interventions. J Am Coll Cardiol 1991;17:26B-31B.

Nishimura Y, Katuta I, Takeda H, et al. Effect of natural chelating agents on the intestinal-absorption of radiostrontium in rats. Radiation Protection Dosimetry 1994:53 (1-4) :331-34.

Rochery M, Lam TM, Crighton JS. FTIR&ATR analyses on a polypropylene (PP) surface after plasma treatment in the study of chitosan surface grafting to improve PP dyeing behavior. Macromol symp 1997; 119:277-82.

Chitin Chemistry by George A.F. Roberts Chapter 4 and Chapter 5, Section 5.2 and 5.3.

* cited by examiner

Chitosan hydrogel coated PET before absorbing phosphoric acid $YPO_4$ precipitation on modified surface CePO₄ precipitation on modified surface

MODIFICATION OF POLYMER SURFACES AS RADIOISOTOPE CARRIERS

BACKGROUND OF THE INVENTION

The present invention relates to surface modification, of polymers to act as carriers of radioisotopes and to encapsulation of the radioactive modified surface, for use in radiation therapy devices, for example.

Within this application several publications are referenced by Arabic numerals within parenthesis. Full citations for these and other publications may be found at the end of the specification immediately preceding the claims. The disclosures of all of these publications in their entireties are hereby incorporated by reference into this application in order to more fully describe the state of the art to which this invention pertains.

Percutaneous transluminal coronary angioplasty is one of the most common current therapies for symptomatic, obstructive atherosclerotic coronary artery and peripheral arterial disease. Unfortunately, a major limitation remains the restenosis rates as high as 30% to 50% with these procedures (1, 2). The limited impact on restenosis achieved with intracoronary stents is due to a greater early gain, with no reduction in late loss, implying a persistent neointimal proliferative response (3, 4).

Applicant have previously illustrated the ability of intravascular sources of ionizing radiation to prevent neointimal proliferation in models of restenosis. The effects of ionizing radiation on cell proliferation and vascular remodeling were previously demonstrated in several animal studies (5–9) and in early clinical trials (10–12). A number of platforms have been devised to deliver brachytherapy for catheter-based systems with high-dose rate: Beta—emitters delivered by catheter-based approaches include $^{90}$Y wire sources (Schneider), encapsulated $^{90}$Sr/Y (Novoste) and $^{32}$P seeds (Guidant), and $^{188}$Re as a solution source for balloon inflation (13). $^{192}$Iridium, a gamma emitter, has been developed in wire-affixed seed geometry (Cordis J&J). For reasons of shielding and patient and operator safety, a clear preference exists for beta sources, although the relative efficacy of various isotopic sources is still under investigation.

Chitin is a cellulose-like biopolymer distributed widely in nature, especially in the crustaceans, insects, fungi and yeast. Its derivative, Chitosan, (1,4)-2-amino-2-deoxy-B-D-glucan, is a natural polymer generally obtained by extensive deacetylation of chitin isolated from crustacean shells. Due to its special biological, chemical and physical properties, chitosan and its derivatives have applications in many industrial, agriculture and biomedical activities as a chelating agent for heavy metal ions (14, 15). Chitosan hydrogels synthesized from chitosan and D, L-lactic acid have been reported in the literature (16, 17). The free amino groups and porous structure of chitosan hydrogels provide them the ability to adsorb o-phosphoric acid (PA) in aqueous solution.

Others have reported forming metallic stents with a Beta emitting source of Rhenium—188 using chelating microfilm having inorganic components (26). However, the prior art does not appear to provide a method of producing an isotope on a polymer layer surface substantially free of inorganic polymers.

SUMMARY OF THE INVENTION

The present invention relates to a novel radiation delivery material which may be useful in a particularly simple brachytherapy delivery system, based on the adsorption of a radioisotope, such as $^{32}$P (o-phosphoric acid), by a polymer layer substantially free of inorganic polymers such as hydrogel, on a polymer surface such as a PET surface. Such prepared PET materials may be used in angioplasty balloons, and could also be used in wire geometry.

The present invention also provides for encapsulating the adsorbed isotope, to keep the adsorbed isotope from eluting off the balloons and contaminating the patient if the radioactive balloons were directly inserted into the vascular system. Encapsulation is desirable even if the wire with attached isotope is inserted into a closed catheter, in case of a leak developing in the catheter. The invention provides means for minimizing the body contamination by isotope leakage. Applicants have determined and interpreted the isotope off-rate for different coatings. Applicants have found that the best results were obtained by coating with a combination of two different polymer solutions. The sample surface was characterized by ATR-FTIR, optical and scanning electron microscopy.

According to one aspect of the invention, a method of making a radioactive source for treating a patient is provided, comprising, forming a polymer layer on a substrate material, the formation being substantially free of inorganic polymers, and exposing the polymer layer to a radioactive isotope so that the radioactive isotope is adsorbed in the layer.

According to another aspect of the invention, a method for making a radioactive source is provided, comprising, forming an organic layer of on a substrate material, and exposing the polymer layer to a radioactive isotope material so that the radioactive isotope material is adsorbed in the layer.

According to another aspect of the invention, a method for making a radioactive source is provided, comprising providing a substrate material, forming a layer of organic polymer on the substrate material, exposing the polymer layer to a radioactive isotope so that the radioactive isotope is absorbed in the layer, and coating the exposed layer to seal the radioactive isotope.

According to another aspect of the invention, a method for making a radioactive source is provided, comprising providing a polymer substrate material, forming a polymer layer on the substrate material and exposing the substrate material to a radioactive isotope so that the radioactive isotope is absorbed in the layer. The invention also provides a product made according to any one of the above described methods.

The invention also provides a radioactive source, comprising a substrate material, a layer of polymer material substantially free of inorganic polymers on the substrate material, and a radioactive isotope adsorbed in the layer.

The invention also provides a radioactive source, comprising a substrate material, a layer of polyer material substantially free of inorganic polymers on the substrate material, a radioactive isotope adsorbed in the layer, and a coating on the layer to seal the radioactive isotope.

The invention also provides a radioactive source, comprising a polymer substrate material, a layer of polymer material on the substrate material, a radioactive isotope adsorbed in the layer, and a coating on the layer to seal the radioactive isotope.

The invention also provides a radioactive source, comprising a polymer substrate material, a layer of polymer material substantially free of inorganic polymers on the substrate material, a radioactive isotope adsorbed in the layers, and a coating on the layer to seal the radioactive isotope.

DESCRIPTION OF THE PREFERRED EMBODIMENTS

Figure 1:
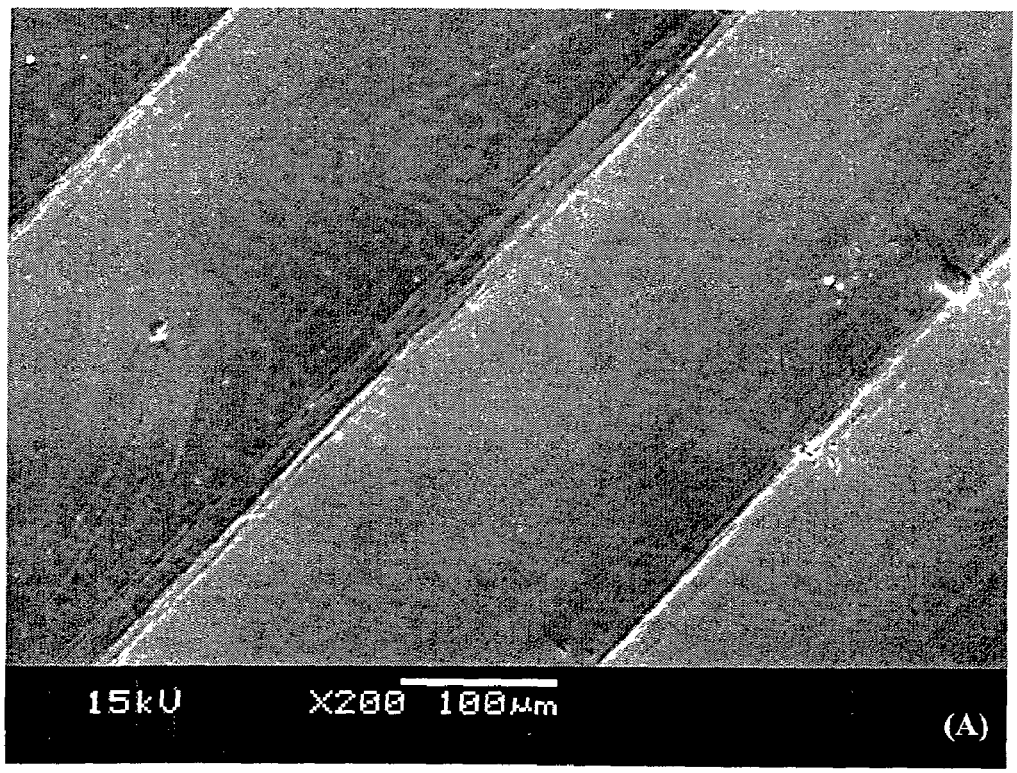
FIG. 1 shows scanning electron microscope (SEM) photographs of (A) oxygen plasma treated PET surface and (B) chitosan hyrogel coated PET surface.
Figure 1:
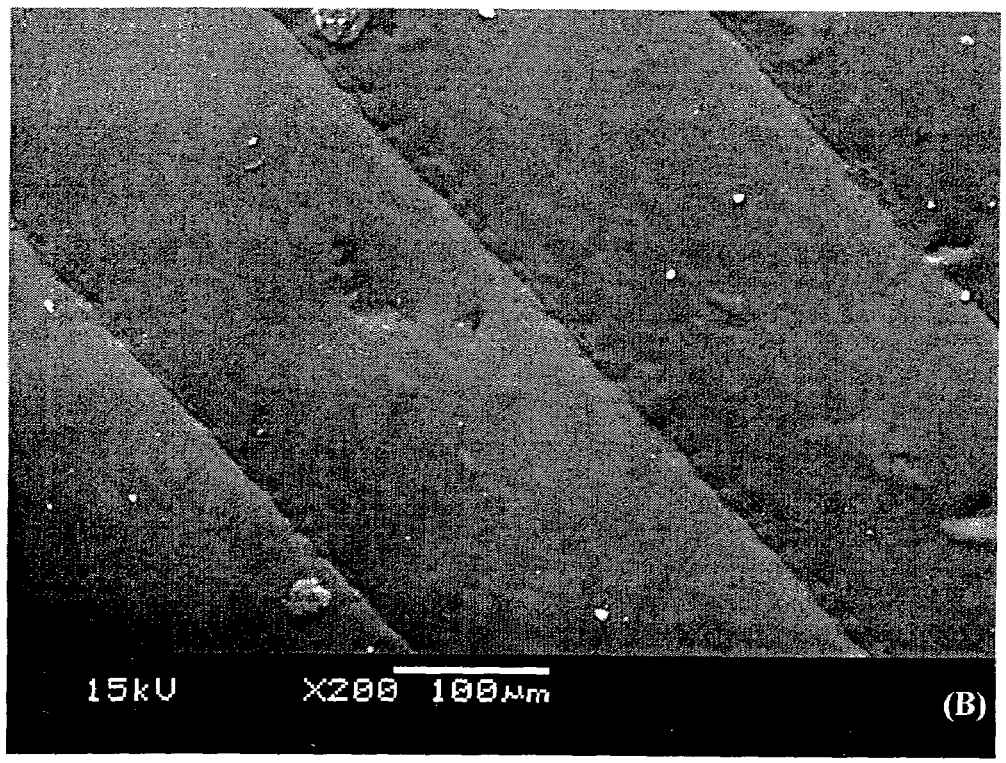

According to one aspect of the invention, a method of making a radioactive source for treating a patient is provided, comprising, forming a polymer layer on a substrate material, the formation being substantially free of inorganic polymers, and exposing the polymer layer to a radioactive isotope so that the radioactive isotope is adsorbed in the layer.

The substrate material may also be provided, and may be a polymer substrate material such as polyethylene terephtalate. The substrate material may be in the form of an inflatable balloon or wire.

The layer of polymer may be hydrogel.

The substrate material may be treated with oxygen plasma to obtain a hydrophilic surface, before the step of forming a polymer layer.

The radioactive isotope may be a radioisotope of $^{32}P$, $^{90}Y$, $^{144}Ce$ or $^{169}Re$.

The exposed layer may be coated with a sealant, for example a polymer sealant, such as a coating of poly (styleneacrylic acid), polyurethane solution, and/or a polyether based aliphatic polyurethane resin.

Preferably, the step of coating comprises coating the exposed layer with an AST-B (poly(stylene-polyurethane)) solution and then coating with a polycarbonate based aliphatic polyurethane solution.

According to another aspect of the invention, a method for making a radioactive source is provided, comprising, forming an organic layer of on a substrate material, and exposing the polymer layer to a radioactive isotope material so that the radioactive isotope material is adsorbed in the layer.

The substrate material may also be provided, and may be a polymer substrate material. The exposed layer may be coated to seal the radioactive isotope.

According to another aspect of the invention, a method for making a radioactive source is provided, comprising providing a substrate material, forming a layer of organic polymer on the substrate material, exposing the polymer layer to a radioactive isotope so that the radioactive isotope is absorbed in the layer, and coating the exposed layer to seal the radioactive isotope.

According to another aspect of the invention, a method for making a radioactive source is provided, comprising providing a polymer substrate material, forming a polymer layer on the substrate material and exposing the substrate material to a radioactive isotope so that the radioactive isotope is absorbed in the layer.

The invention also provides a product made according to any one of the above described methods.

The invention also provides a radioactive source, comprising a substrate material, a layer of polymer material substantially free of inorganic polymers on the substrate material, and a radioactive isotope adsorbed in the layer.

The invention also provides a radioactive source, comprising a substrate material, a layer of polyer material substantially free of inorganic polymers on the substrate material, a radioactive isotope adsorbed in the layer, and a coating on the layer to seal the radioactive isotope.

The invention also provides a radioactive source, comprising a polymer substrate material, a layer of polymer material on the substrate material, a radioactive isotope adsorbed in the layer, and a coating on the layer to seal the radioactive isotope.

The invention also provides a radioactive source, comprising a polymer substrate material, a layer of polymer material substantially free of inorganic polymers on the substrate material, a radioactive isotope adsorbed in the layers, and a coating on the layer to seal the radioactive isotope.

Materials and Methods

Chitosan (Mw=150 kD) from Fluka (Switzerland) and D, L-lactic acid (85%) from Fisher Scientific (USA) were used for preparation of chitosan hydrogel layer. O-phosphoric acid (85%) (Fisher Scientific) was used for adsorption. $YCl_3$ and $CeCl_3$ from Sigma (USA) were used for deposition. P-o-phosphoric acid (8500–9120 Ci/mmol, 10 mCi/ml) and Yttrium-90 radionuclide (~500 Ci/mg, >500 mCi/ml) (NEN) were used for measuring adsorption efficiency and kinetics by liquid scintigraphy. Ecoscint A was obtained from National Diagnostics Inc. (USA). PET balloons (15 mm×55 mm) were obtained from Advanced Polymers Inc. (USA). The AST-A(poly(styrene-acrylic acid)) solution, AST-B (polyurethane) solution and crosslinker solutions for coating were obtained from Advanced Surface Technology Inc. (USA). Tecoflex resin (polyether based aliphatic polyurethane) and Carbothane resin (polycarbonate based aliphatic polyurethane) were obtained from Thermedics Inc. (USA). All coatings are medical grade and used for biomeedical applications. Ecoscint A from National diagnostics Inc. (USA) was used as the scintillation solution.

Surface Modification of PET Balloons by Chitosan Hydrogel (PET) Poly(ethyleneterephtalate) balloons were treated by oxygen plasma to obtain hydrophilic surfaces. The PET balloons were then cut to small pieces (5 mm×10 mm, thickness 30±2 um). These PET films were coated on one side surface by 1% chitosan/D, L-lactic acid solution, which was prepared by dissolving chitosan powder in D,L-lactic acid acqueous solution with the weight ratio of chitosan/lactic acid=½. The coated films were dried in an oven at 80° C. for 1 hour. The thickness of the coated films was 31±2 um.

Adsorption of Phosphoric Acid by Hydrogel Layer ($^{32}P$ Variation)

Coated films were immersed in 0.2 mMPA aqueous solutions (0.5 ml) with certain amount of $^{32}P$ radio isotope at room temperature or at 50° C. The radioactivity of $^{32}P$ on the surface may be computed by measuring the residual $^{32}P$ in the adsorbing solution with a liquid scintillation counter (LSC). The adsorption efficiency and kinetics were computed by measuring the residual $^{32}P$ in the adsorbing solutions. Adsorption efficiency of samples at time t was calculated by following equation:

$$\text{Adsorption Efficiency (\%)}=(M_0-M_t)/M_0(x100),$$

where $M_0$ and $M_t$ are the amount of PA in solutions before the adsorption ($M_0$) and after the adsorption at the time t ($M_t$). In general, about 500 uCi isotope was absorbed on the surface of each sample.

Precipitation of Adsorbed Phosphoric Acid and Sealing by Polyurethane Coatings

The films after adsorption were suspended in freshly prepared saturated $Ca(OH)_2$/5% $CaCl_2$ solution for 5 minutes. The adsorbed PA precipitated in the hydrogel and forms a complex with chitosan. The films were then dip-coated in poly(stylene-acrylic acid) and different polyurethane solutions (some with 3% crosslinker) and dried. The second layer was coated on the surface after the first layer dried thoroughly. After the treatment, the films were washed with phosphate buffer (PBS) and distilled water. The thickness of coated films is about 55±2 um. The off-rate of samples in PBS at 37° C. was computed by measuring the released $^{32}P$ in PBS with liquid scintillation counter (LSC). The off-rate of samples at time t was calculated by following equation:

$$^{32}P \text{ isotope off-rate(\%)}=M_t/M_0(x100),$$

where $M_0$ and $M_t$ are the amount of PA on samples before the releasing ($M_0$), and in PBS after the releasing at time t ($M_t$).

Deposition of $YPO_4$ and $CePO_4$ on Sample ($^{90}Y$ and $^{44}Ce$ Variations)

The films after adsorption were suspended in $YCl_3$ and $CeCl_3$ solutions. The $YPO_4$ and $CePO_4$ were precipitated on sample surface. The films were then dip-coated in poly(stylene-acrylic acid) and different polyurethane solutions (some with 3% crosslinker) and dried. The second layer was coated on the surface after the first layer dried thoroughly. After the treatment, the films were washed with phosphate buffer (PBS) and distilled water.

Characterization

For the $^{32}P$ variation, Fourier Transform Infrared Transmission (FTIR) spectra were obtained using the attenuated total reflection technique (ATR), and the surfaces were analyzed on a Perkin-Elmer 2000 Infrared Fourier transform spectrometer.

For all variations, scanning electron microscopy (SEM) analyses were carried out using a Jeol JSM-5600LV scanning electron microscope (Japan). The sample was mounted on metal stubs and sputter-coated with gold-palladium. An MTI 3CCD digital camera on a Zeiss Axiover 100 optical microscope may be used to investigate the sample morphology before drying. A liquid scintillation counter from LKB Wallace, 1209Rackbeta, was used to measure the concentration of the $^{32}P$ tope before and after the adsorption, and of the $^{90}Y$ isotope in the solution before and after the deposition. 10 ul solution was taken and mixed with 5 ml scintillation solution. The thickness of the sutures was measured by a micrometer caliper.

Chitosan Hydrogel Layer PET Balloon

Figure 2:
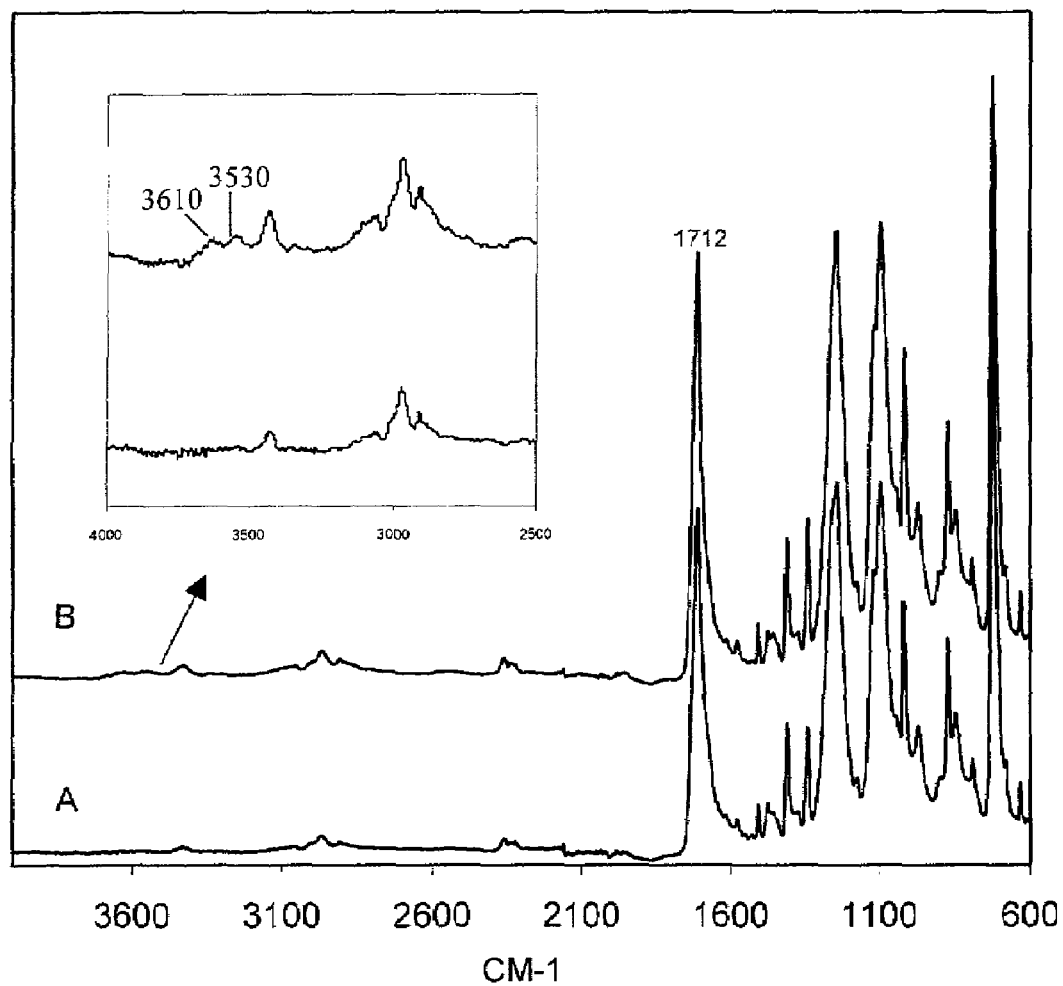
FIG. 2 shows ATR-FTIR spectra of (A) untreated PET surface and (B) oxygen plasma treated PET surface.
Figure 3:
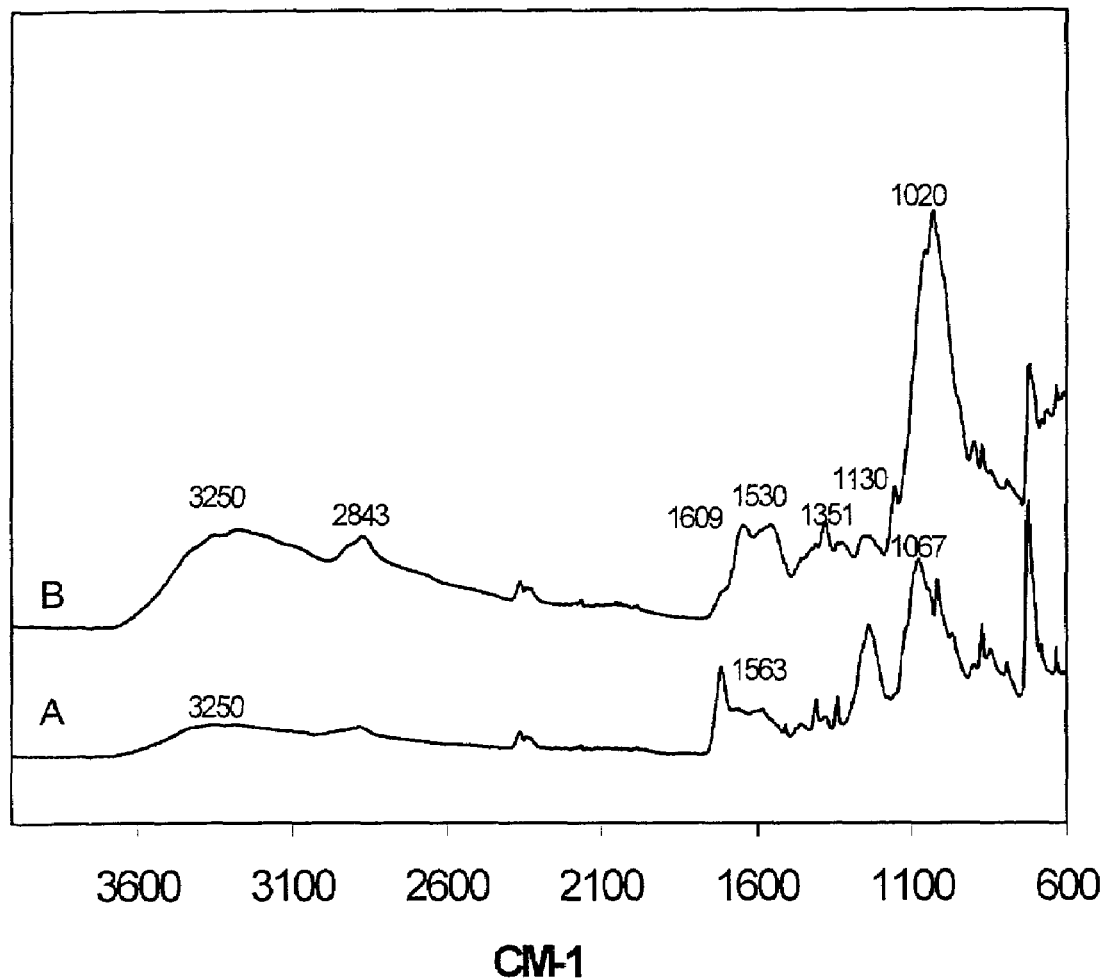
FIG. 3 shows ATR-FTIR spectra of (A) chitosan hyrogel coated PET surface, (B) the coated PET surface after adsorption in 2 mM phosphoric acid solution for 2 hours.
Figure 4:
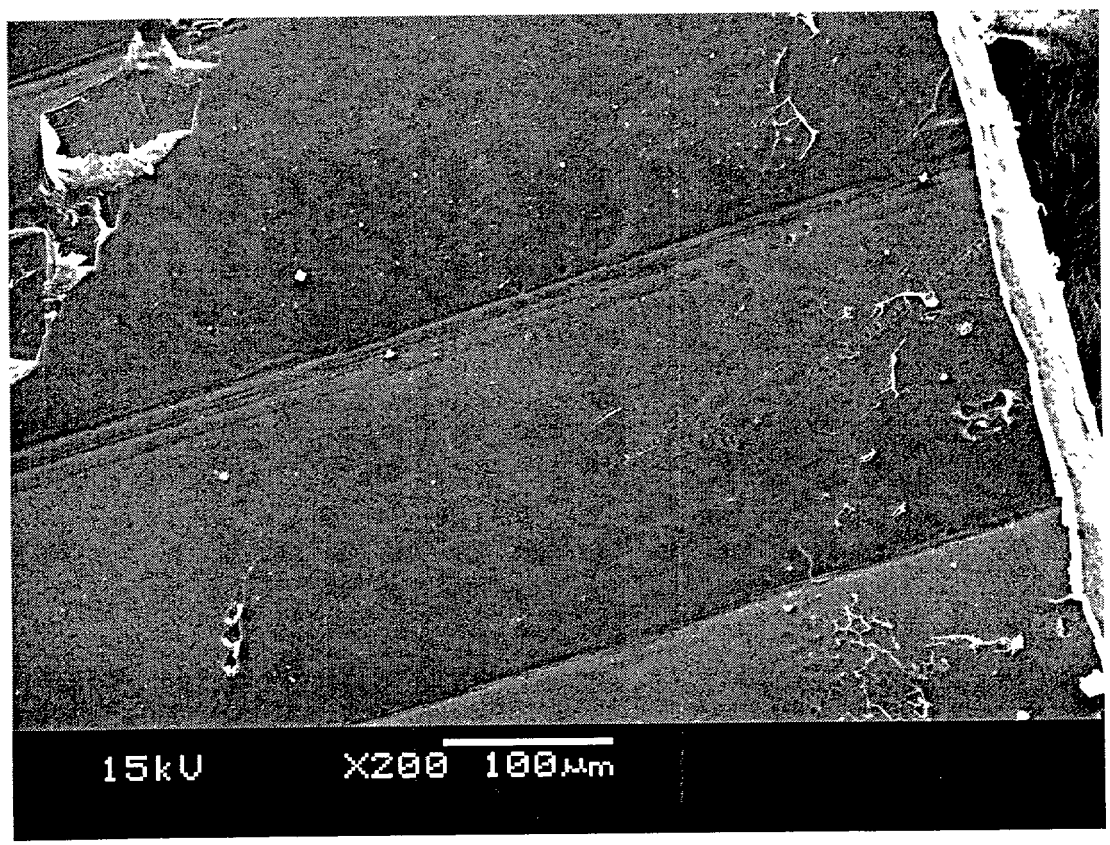
FIG. 4 shows scanning electron microscope (SEM) photographs of chitosan hydrogel coated PET balloon surface after adsorption in phosphoric acid solution for 2 hours.

Untreated PET balloon surface is hydrophobic. After oxygen plasma treatment, the surface becomes hydrophilic. FIG. 1A shows the morphology of the plasma treated PET film. The parallel lines on the surface reflect the manufacturing process. After coating with chitosan hydrogel, the PET film became much smoother and a thin layer, of about 1 um, appeared on the surface (FIG. 1B). FIG. 2 shows the ATR-FTIR spectra of the untreated and oxygen plasma treated PET film. Compared to the spectrum of untreated sample in FIG. 2A, the oxygen plasma treated sample (FIG. 2B) has two new small peaks appearing at 3610 $cm^{-1}$ and 3530 $cm^{-1}$ which are due to the —COOH and —OH groups formed on the surface by oxygen plasma treatment. As shown in FIG. 3A, these two peaks were overlapped by a broad peak at 3250 $cm^{-1}$ assigned to the chitosan hydroxyl groups, after the chitosan hydrogel was coated on the surface. In addition, a new peak corresponding to free amino groups of chitosan appeared at 1563 $cm^{-1}$ and the peak at 1067 $cm^{-1}$ was assigned to the chitosan saccharide structure.

Figure 10:
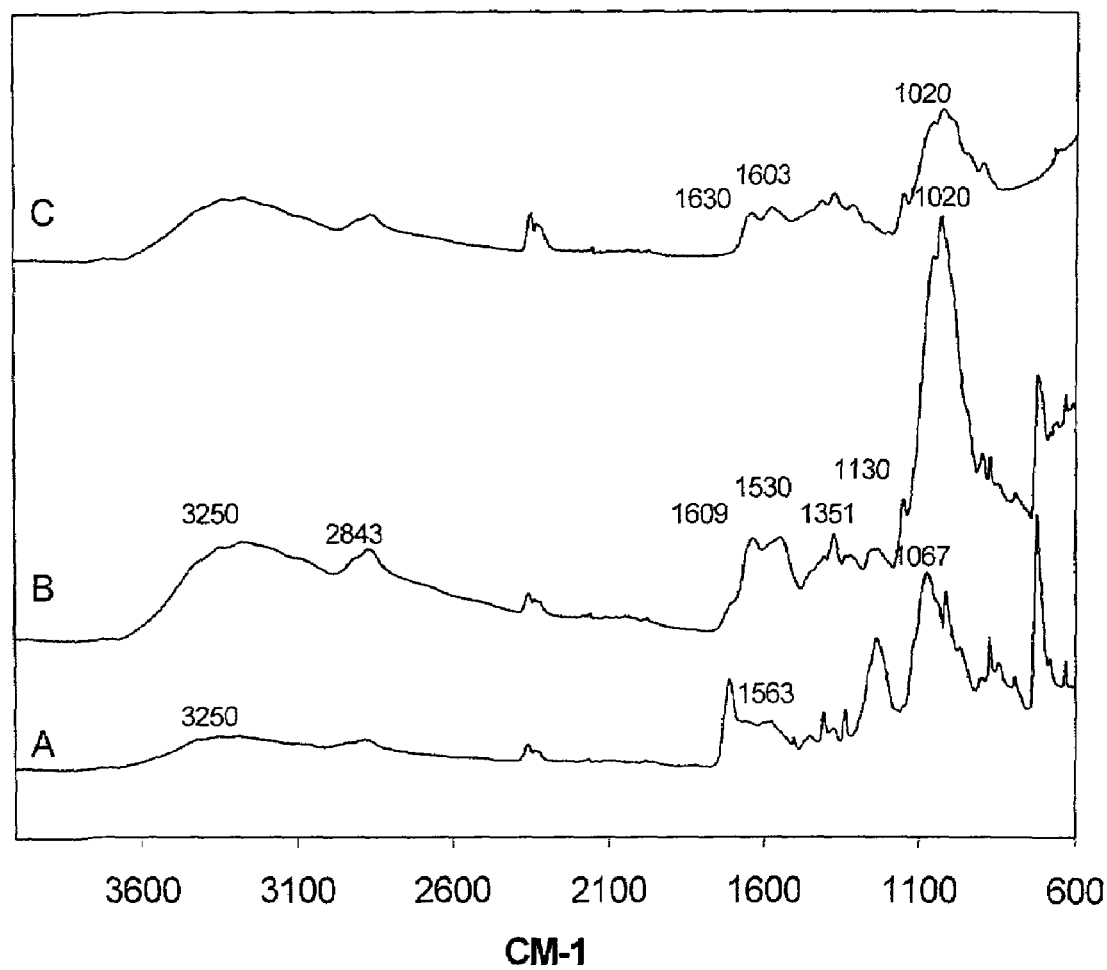
FIG. 10 shows ATR-FTIR spectra of (A) chitosan hyrogel coated PET balloon surface, (B) the sample after adsorption in phosphoric acid solution and (C) after further soaking in saturated $Ca(OH)_2/5\%$ $CaCl_2$ solution.
Figure 11:
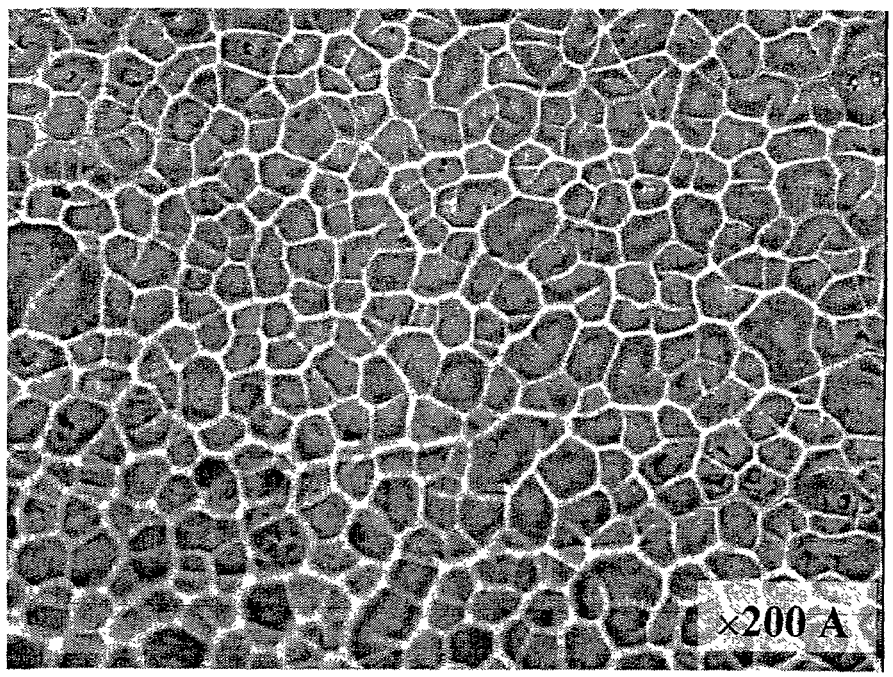
FIG. 11 shows optical microscope photographs of (A) the sample after adsorption in phosphoric acid solution (x200) and (B) after further soaking in saturated $Ca(OH)_2/5\%$ $CaCl_2$ solution (x200)
Figure 11:
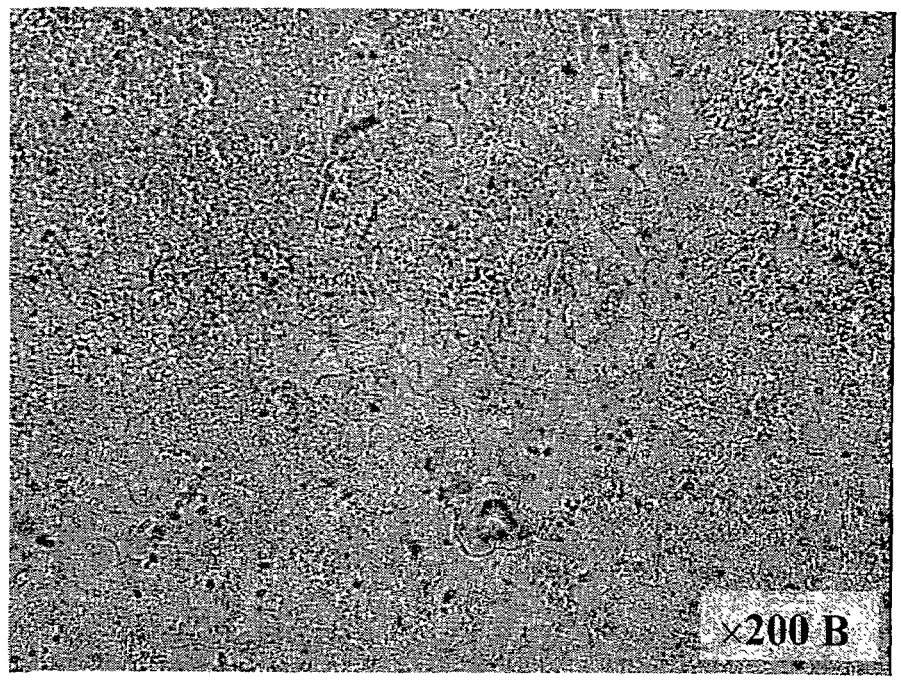

The chitosan hydrogel coated film was immersed in 2 mM phosphoric acid solution for 2 hours and dried, and the ATR-FTIR spectrum of the sample surface was measured (FIG. 10B). Two new and strong peaks (1609 $cm^{-1}$ and 1530 $cm^{-1}$), that are related to the deformation of $NH_3$+groups in chitosan appeared in the spectrum. (FIG. 11B). The —$PO_4$ vibration peaks are predominant compared to the existing chitosan peaks. The absorption peaks at 1130 $cm^{-1}$ and 1020

$cm^{-1}$ are due to the P—O stretch. In addition, the peak of hydroxyl group at 3250 $cm^{-1}$ increased after forming the chitosan phosphate.

Precipitation of Adsorbed Phosphoric Acid

Figure 9:
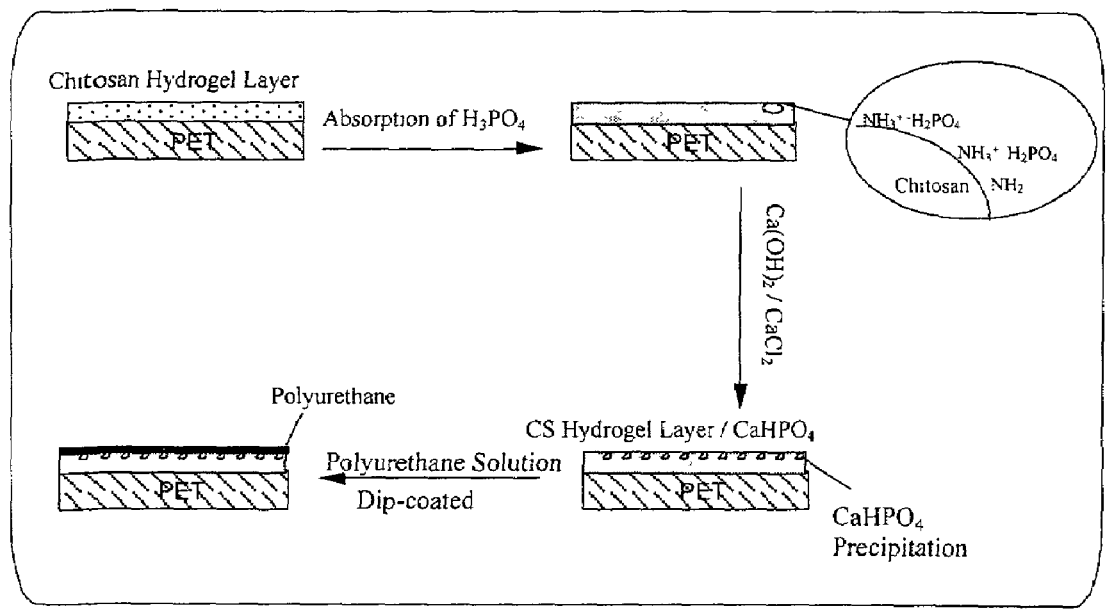
FIG. 9 shows encapsulation of isotope on B-emitting PET balloon surface.

The coated film, with adsorbed $H_3PO_4$, was soaked in saturated $Ca(OH)_2$/5% $CaCl_2$ solution for 5 minutes. Calcium phosphate ($CaHPO_4$), which is insoluble to some extent in neutral and basic aqueous solutions, was precipitated and formed a complex with chitosan on the surface as shown in FIG. 9. The ATR-FTIR spectrum (FIG. 10C) has a broad pattern of poorly crystalline calcium phosphate with 1130 $cm^{-1}$ and 1020 $cm^{-1}$ peaks which ascribed to the P—O stretch and are present along with the other chitosan peaks.

Figure 12:
FIG. 12 shows scanning electron microscope (SEM) photographs of sample after soaking in saturated $Ca(OH)_2/5\%$ $CaCl_2$ solution and (A)x200 and (B)x2000.
Figure 12:
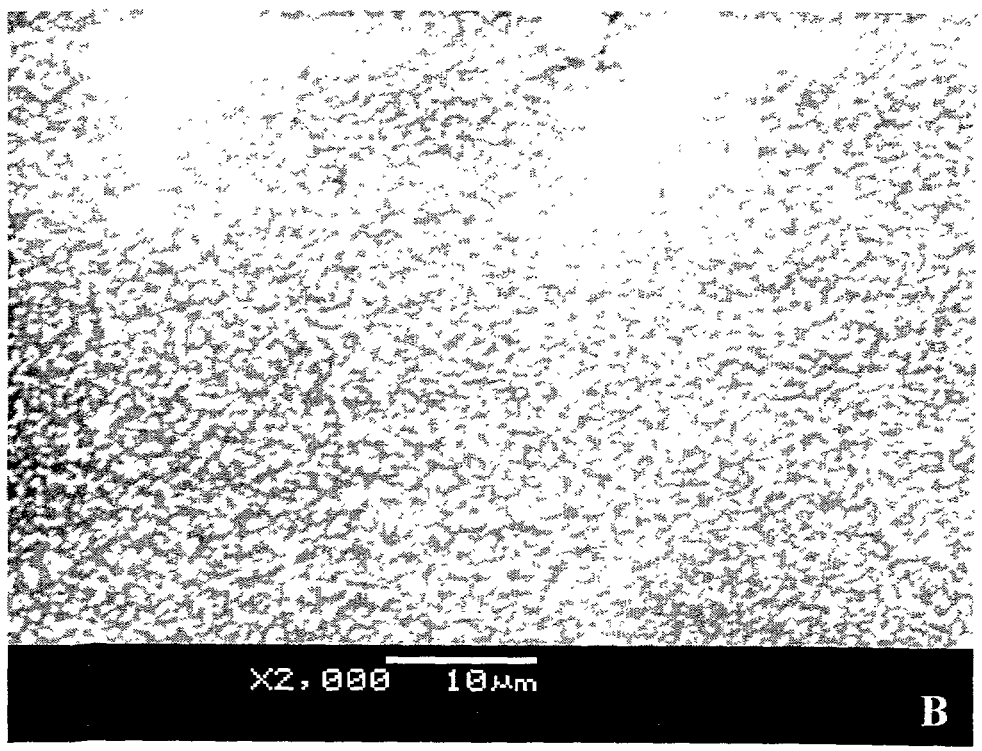
Figure 13:
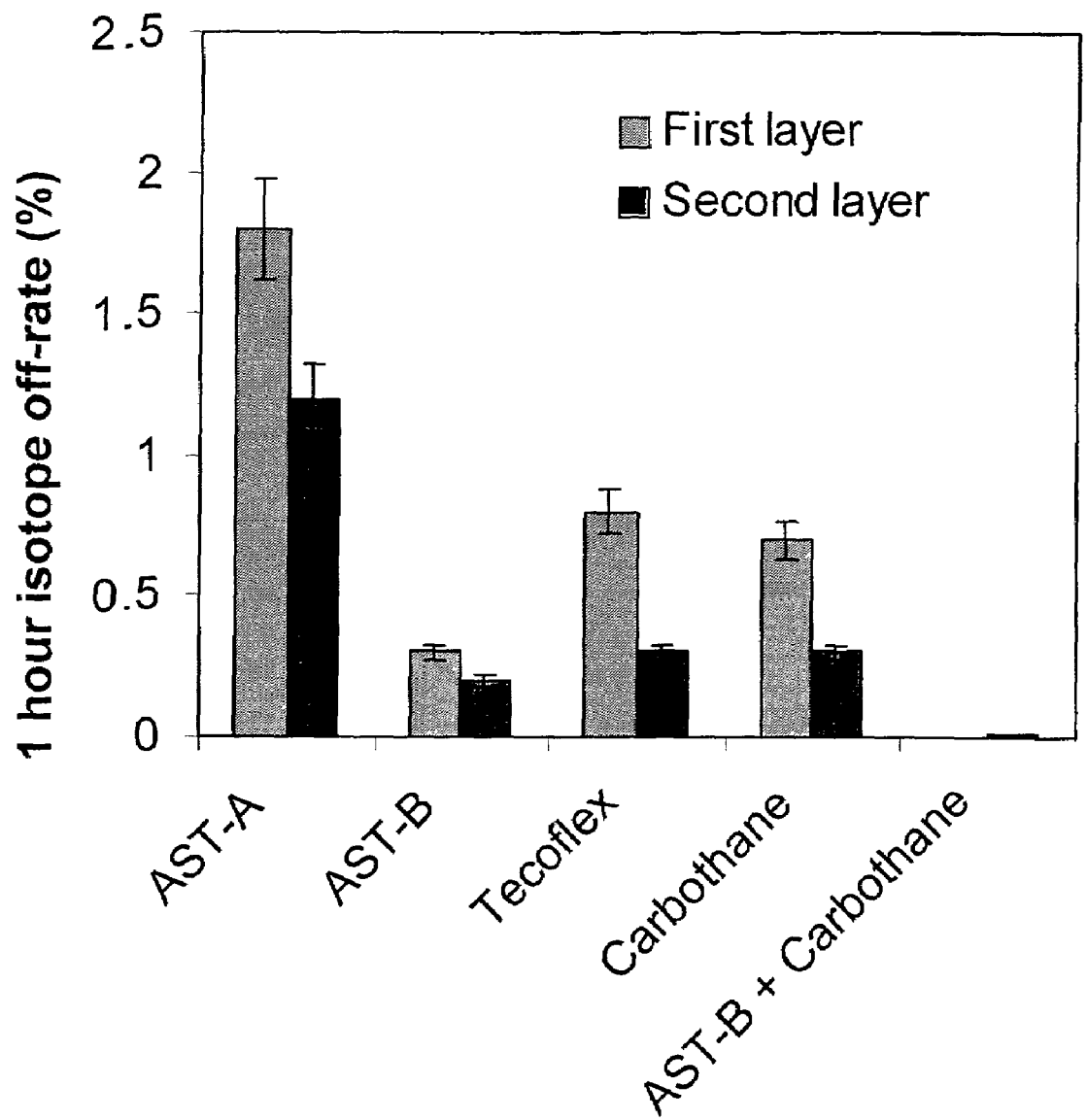
FIG. 13 shows 1 hour isotope off-rate of samples encapsulated by different polymer layers.

The morphology of samples before and after $CaHPO_4$ precipitation investigated by both optical and scanning electron microscope. The coated sample after absorbing phosphoric acid was directly used for optical microscopy before drying. As shown in FIG. 11A, the chitosan hydrogel on surface swelled extensively, and divided into many small pieces due to the internal intention during the swelled extensively, and divided into many small pieces due to the internal intention during the swelling. After $CaHPO_4$ was precipitated on surface, the swelling of hydrogel decreased significantly and the surface became rough with some small particles on it (FIG. 11B) The SEM photographs of sample after $CaHPO_4$ precipitation is shown in FIG. 12, a coating of fine white particles formed on the surface with the diameter of 1 um or less. The upper left corner of FIG. 12 shows that it was wiped off due to the handling. During the precipitation process, a small amount of $^{32}P$-isotope was released in to PBS that could be ignored compared to $^{32}P$ remained on the surface.

Adsorption Efficiency of Chitosan Hydrogel Layer

Figure 5:
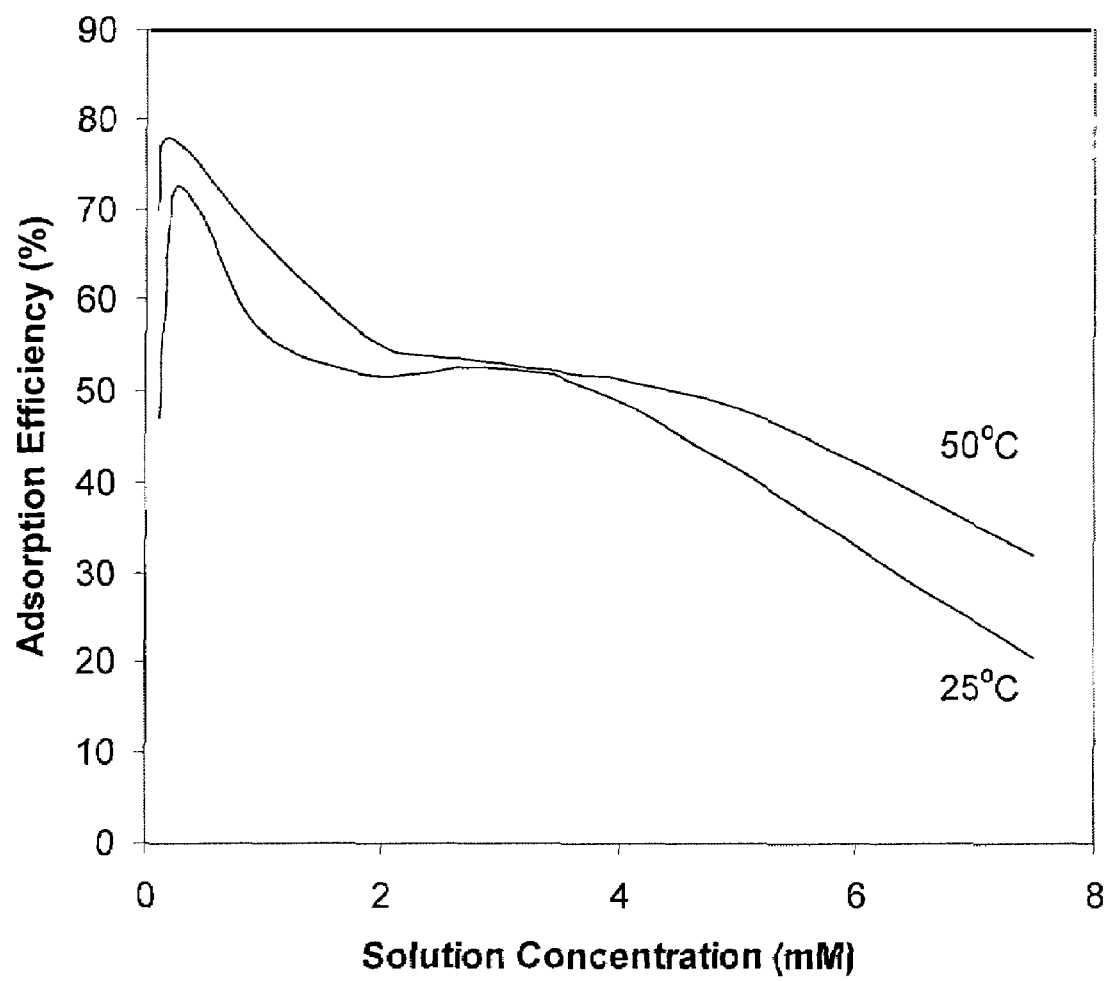
FIG. 5 shows the effect of temperature and solution concentration on sample adsorption efficiency.
Figure 6:
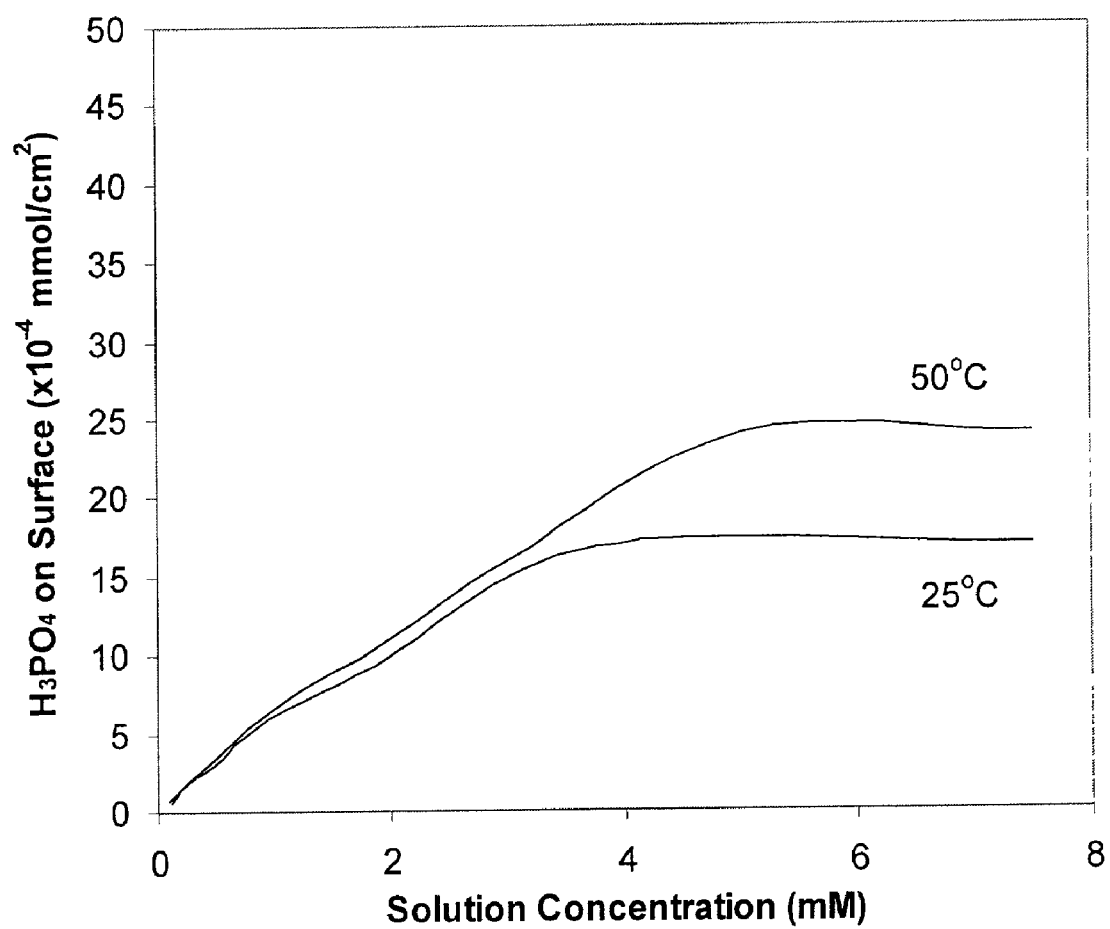
FIG. 6 shows the effect of temperature and solution concentration on the amount of phosphoric acid adsorbed on the sample surface.

The phosphoric acid adsorption efficiency of the treated PET surface was examined at room temperature and at 50° C. as a function of phosphoric acid concentrations. All data were measured after the samples immersed in the solutions for 2 hours. As shown in FIG. 5, the adsorption efficiency of PA increases with the decrease of solution concentration and reaches the maximal at 0.2 mM. In general, the efficiency values at 50° C. are higher than those values at room temperature, while two curves have the same trend. The amount of $H_3PO_4$ adsorbed on the sample surfaces is shown in FIG. 6, which increases with the increase of the solution concentration. Both curves level off at 5 mM due to the saturation of $H_3PO_4$ adsorbed on sample surface. The film adsorbed more $H_3PO_4$ at higher temperature.

Figure 7:
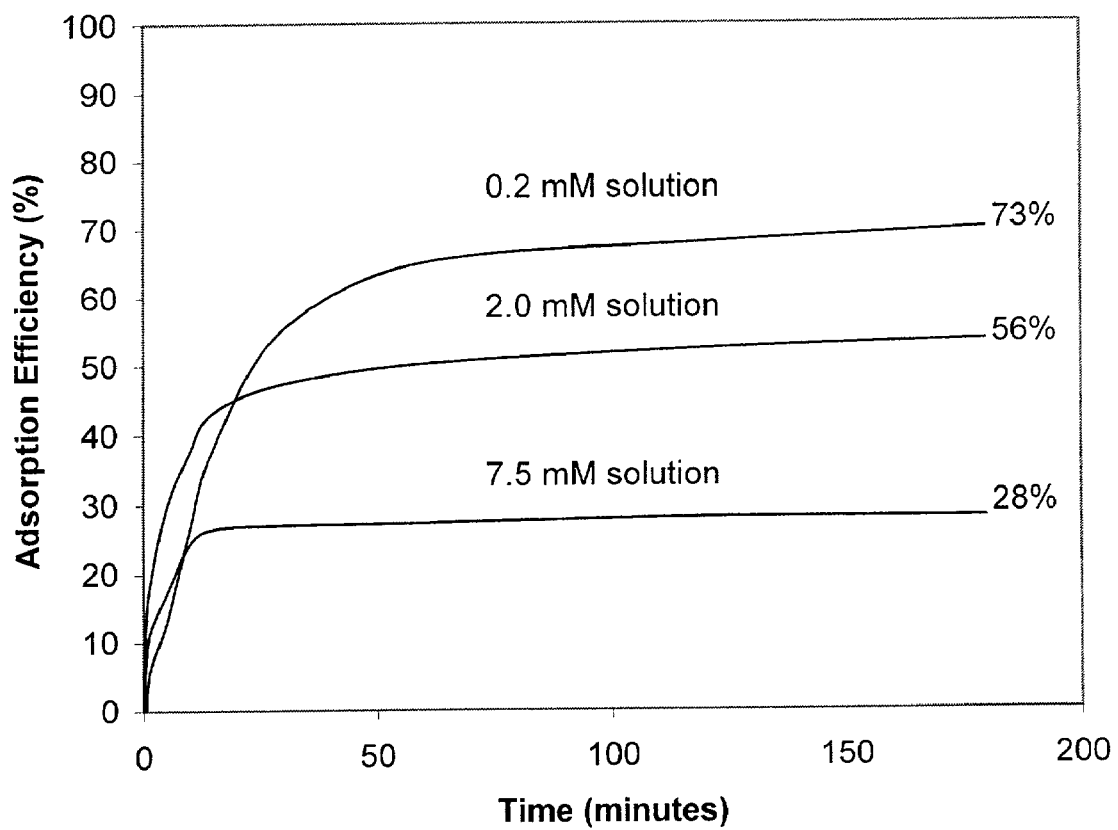
FIG. 7 shows the adsorption kinetics of samples in the phosphoric acid solutions with different concentrations at room temperature.

FIG. 7 presents the adsorption kinetics of samples in different PA concentrations at room temperature. The adsorption efficiency depends notably on the solution concentration and the adsorption time. The higher the concentration of PA solutions, the adsorption efficiency is lower, but the time to equilibrium is much shorter. In all cases, the equilibrium adsorption was almost reached within 2 hours.

Encapsulation of Isotope by Polymer Layers

In order to prevent leakage of the isotope into the patient, several hydrophobic coatings (Medical grade) were applied on the sample surface by dip-coating method. The details of chosen solutions are described in Table 1.

After the phosphoric acid adsorption and precipitation, the samples were coated one or two layers with different polymer solutions. The films were washed with PBS, distilled water and dried. Only the spectra of polymer layers were recorded in ATR-FTIR, which indicated the total coverage of surface (Data not shown). The results of sample off-rate after 1 hour in PBS was computed by measuring the released $^{32}P$ in PBS with liquid scintillation counter (as shown in FIG. 5). The 1 hour off-rate of all samples with same polymer layer ranges from 0.2% to 2%. As compared to one layer, two layers significantly decrease the isotope off-rate due to the increase of layer thickness. The best results were obtained when the sample was coated first with AST-B and then with Carbonate. The isotope off-rate of double-coated sample decreased to 0.01% after 1 hour immersion in PBS.

Table 2 shows the off-rate of isotope with different treatments. The sample after $^{32}P$ adsorption released 40% of $^{32}P$-PA after 1 hour and almost 90% released after 24 hours. When the surface was treated by $Ca(OH)_2$, the off-rate of $^{32}P$-PA decreased to 15% after 1 hour and 40% after 24 hours. When the sample was coated with polyurethane layers, the hydrophobic coatings could efficiently prevent the water penetrating and dissolve of $CaHPO_4$. The 1 hour off-rate of isotope is about 0.3% and 24 hours off-rate is about 2%. The best results were also obtained when the sample was coated first with AST-B and then with Carbonate. The isotope off-rate of double-coated sample decreased to 0.01% after 1 hour and 0.1% after 24 hours immersion in PBS.

Figure 14:
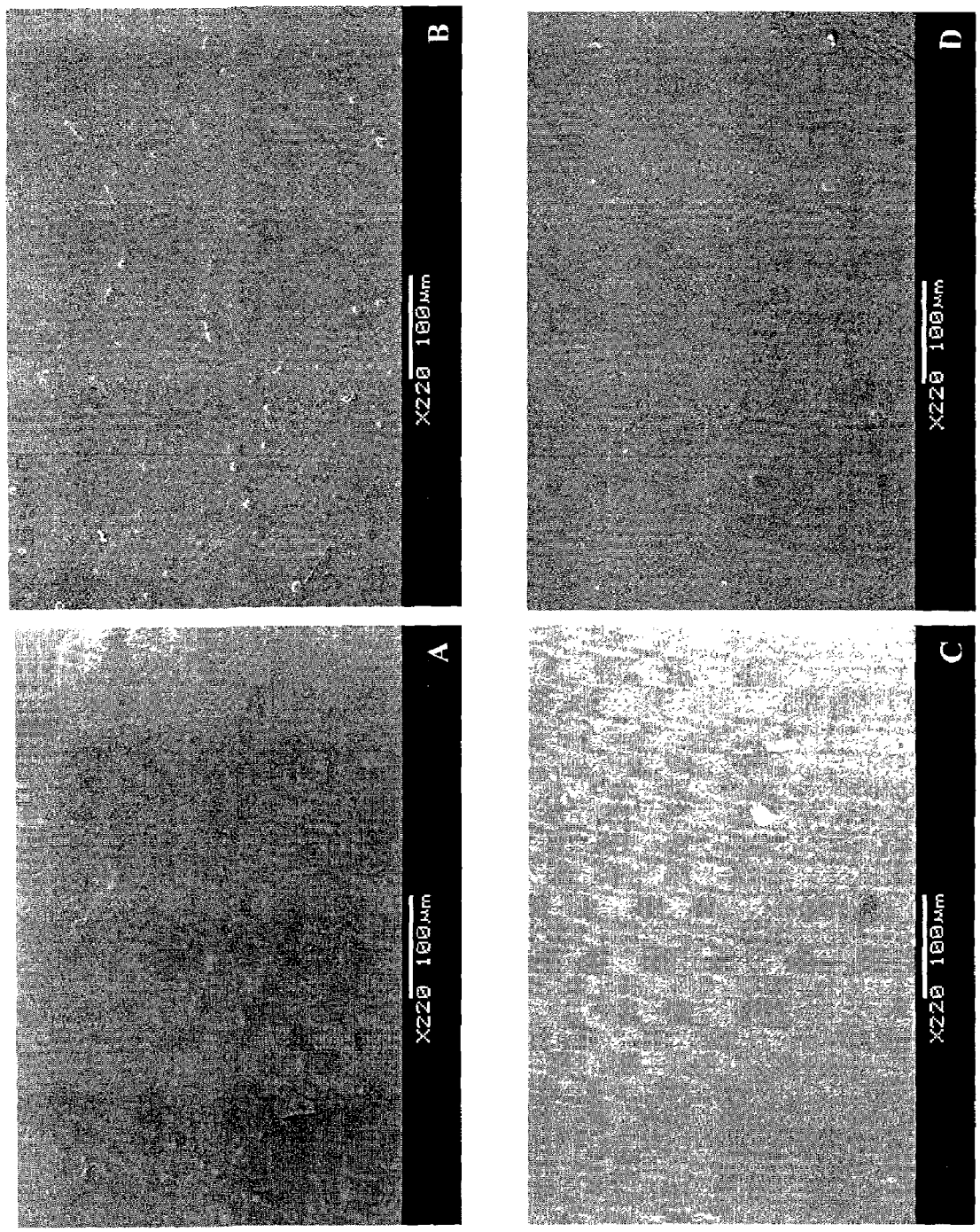
FIG. 14 shows scanning electron microscope (SEM) photographs of samples encapsulated by (A) Tecoflex, (B) Carbonate, (C) AST-B, and (B) AST-B/Carbonate.
Figure 15:
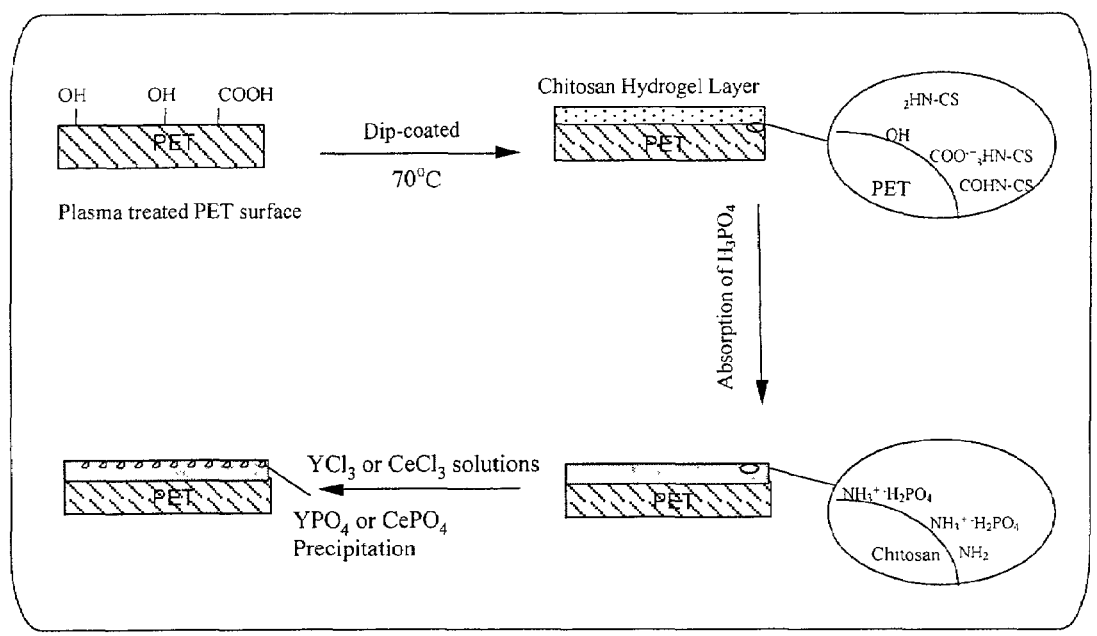
FIG. 15 shows precipitation of $YPO_4$ and $CePO_4$ on the poly(ethylene terephtalate) film surface.
Figure 16:
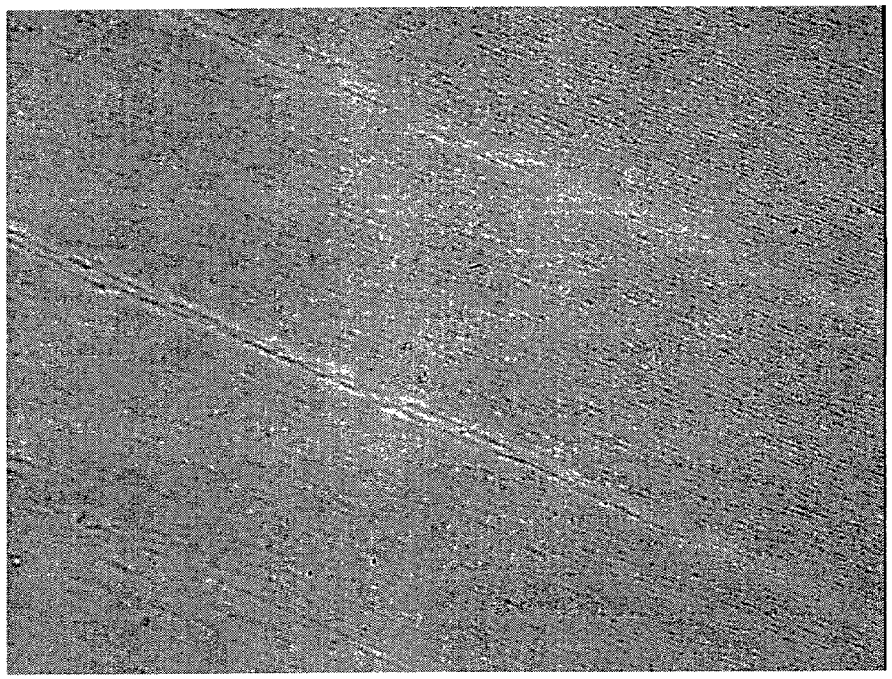
FIG. 16 shows optical microscope photographs of (A) chitosan hydrogel coated PET before absorbing phosphoric acid, (B) $YPO_4$ precipitation on modified surface, and (C) $CePO_4$ precipitation on modified surface.
Figure 16:
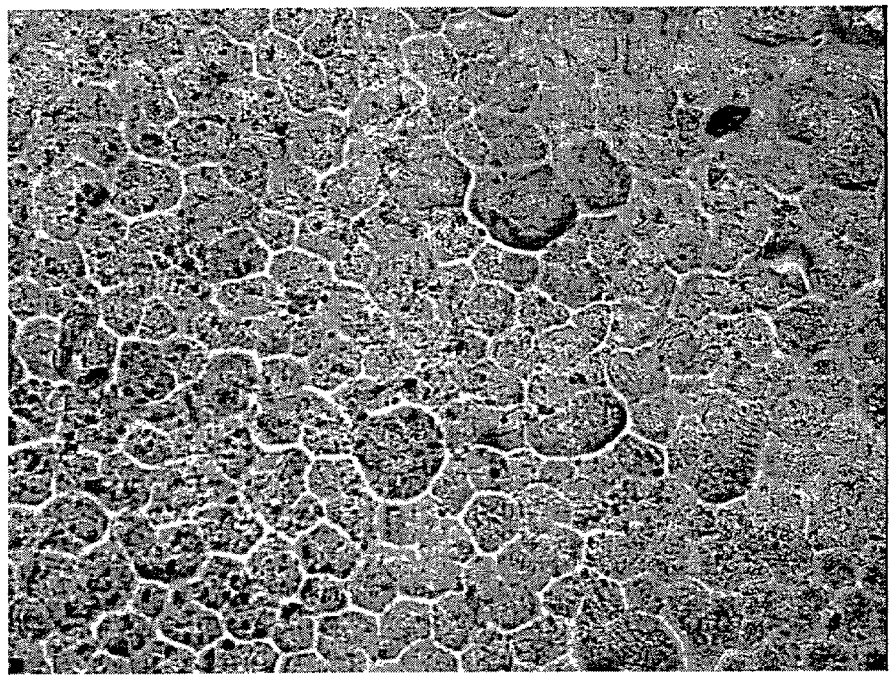
Figure 16:
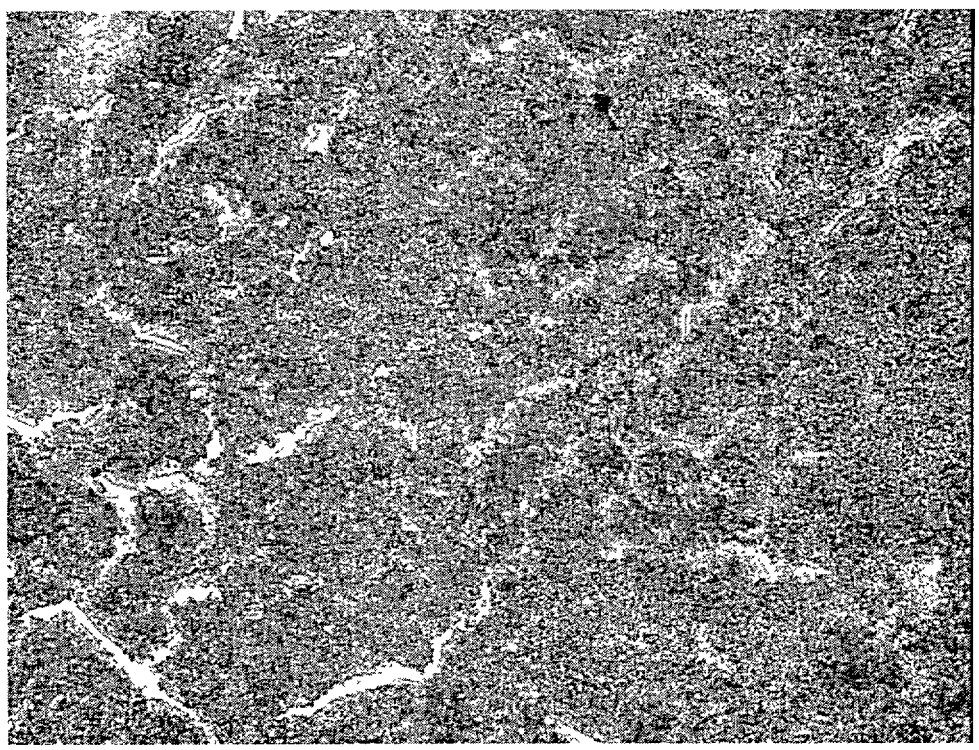
Figure 17:
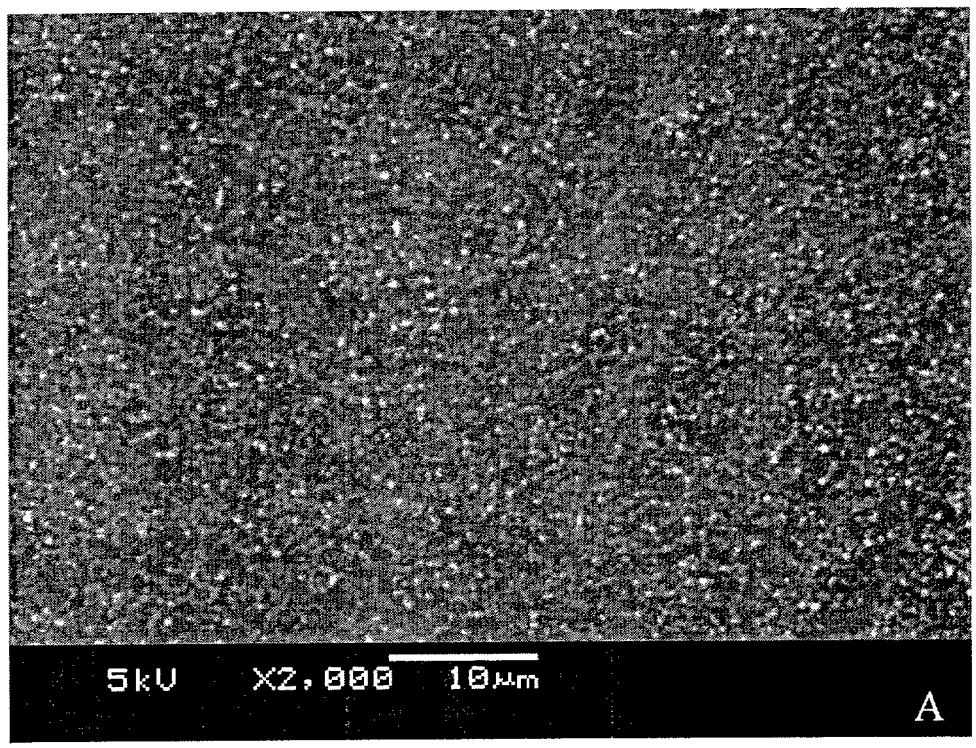
FIG. 17 shows scanning electron microscope (SEM) photographs of samples (A) after soaking in 0.5M $YCl_3$ solution x2000, and (B) after soaking in 2.0M $YCl_3$ solution x2000.
Figure 17:
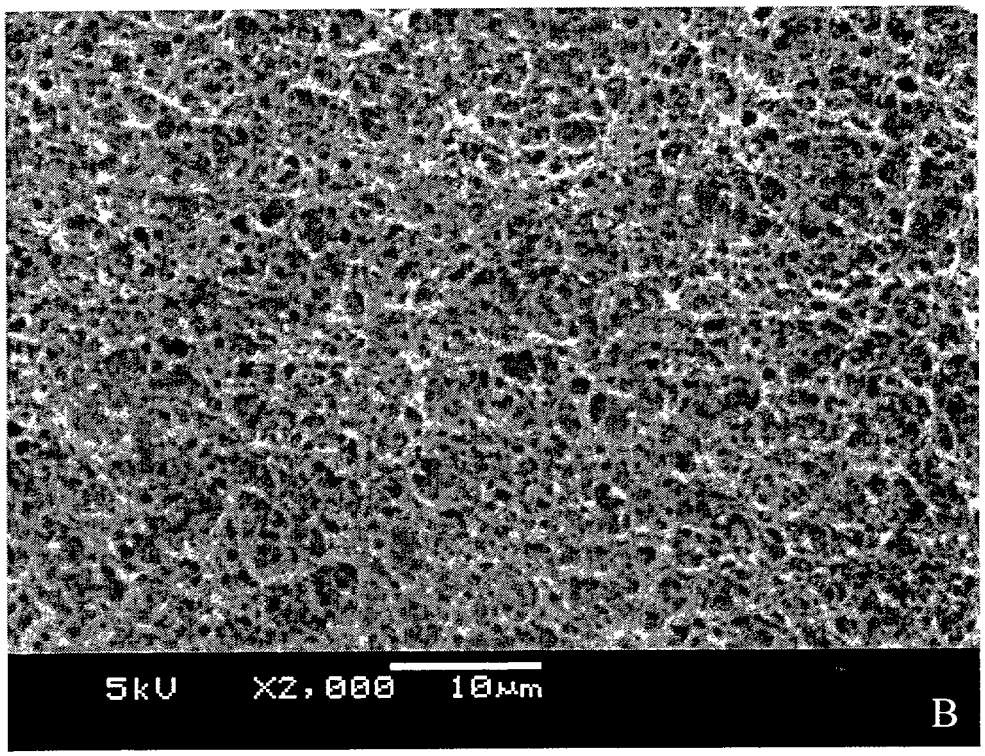
Figure 18:
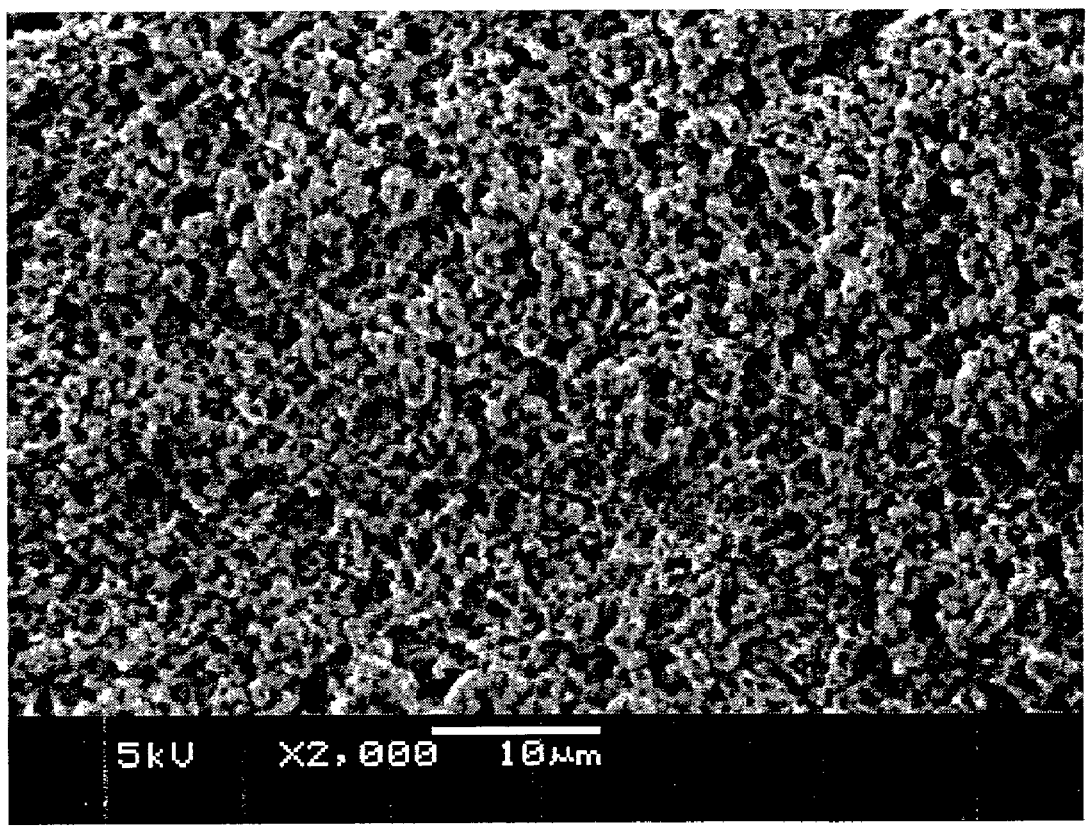
FIG. 18 shows scanning electron microscope (SEM) photographs of a samples after soaking in $CeCl_3$ solution x2000.
Figure 19:
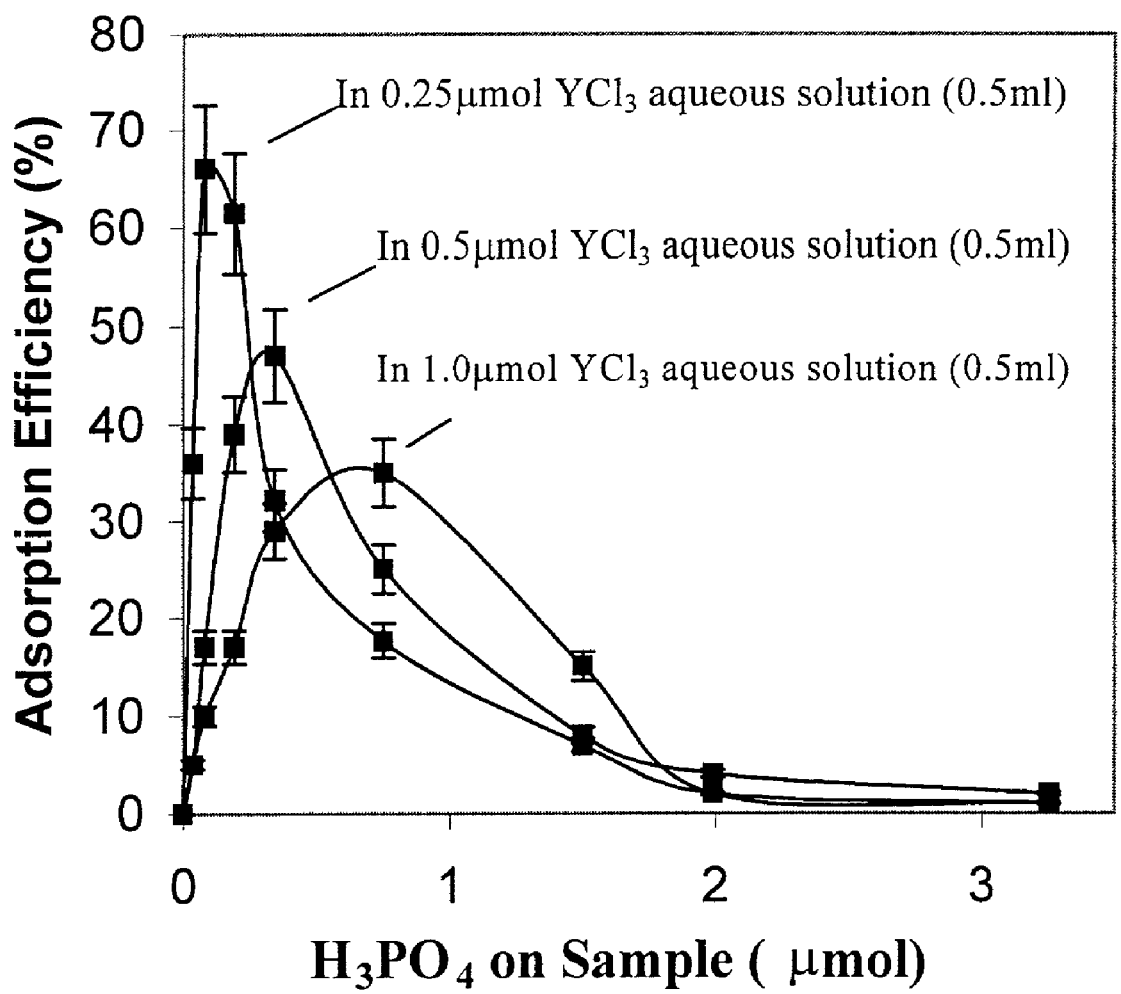
FIG. 19 shows effect of absorbed $H_3PO_4$ on $YPO_4$ deposition efficiency on sample surface.
Figure 20:
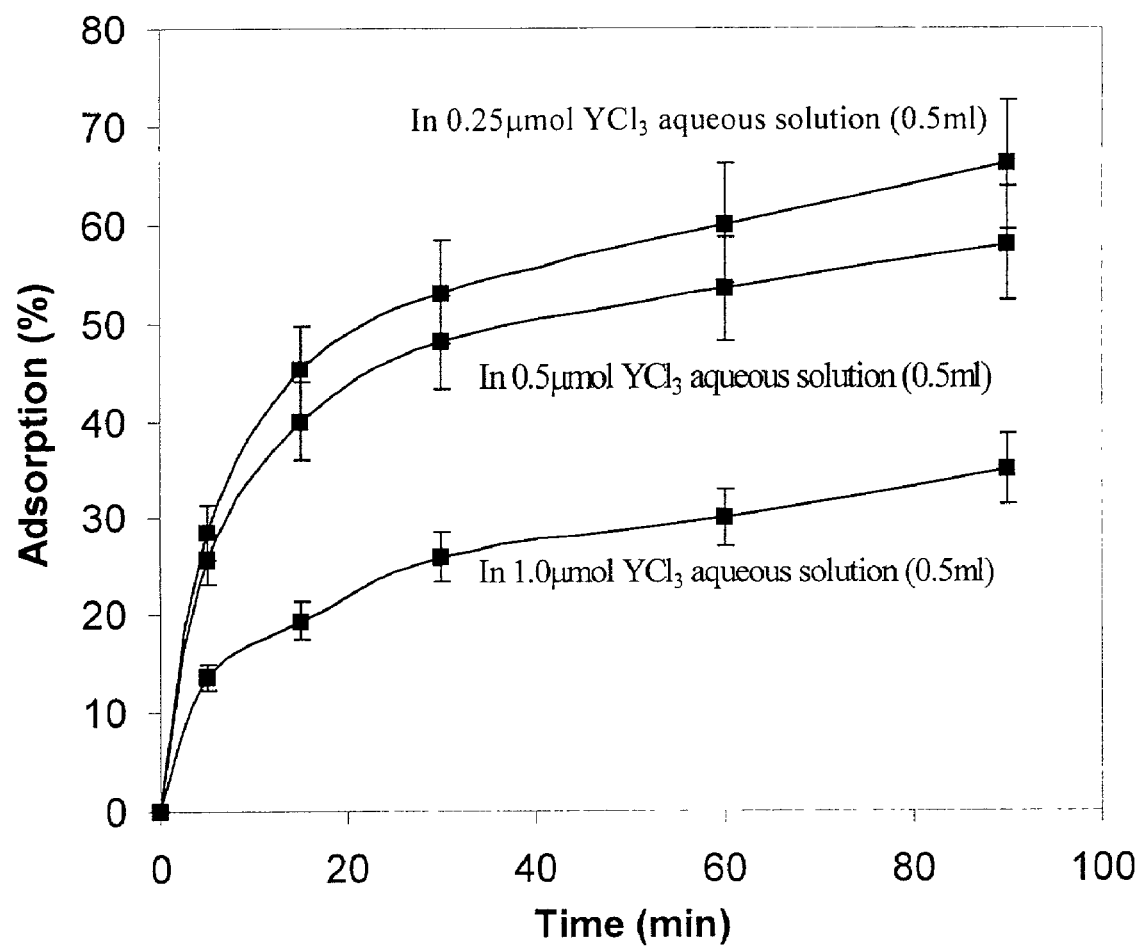
FIG. 20 shows the deposition kinetics of $YPO_4$ deposition efficiency on sample surface in $YCl_3$ solutions with different concentrations.
Figure 21:
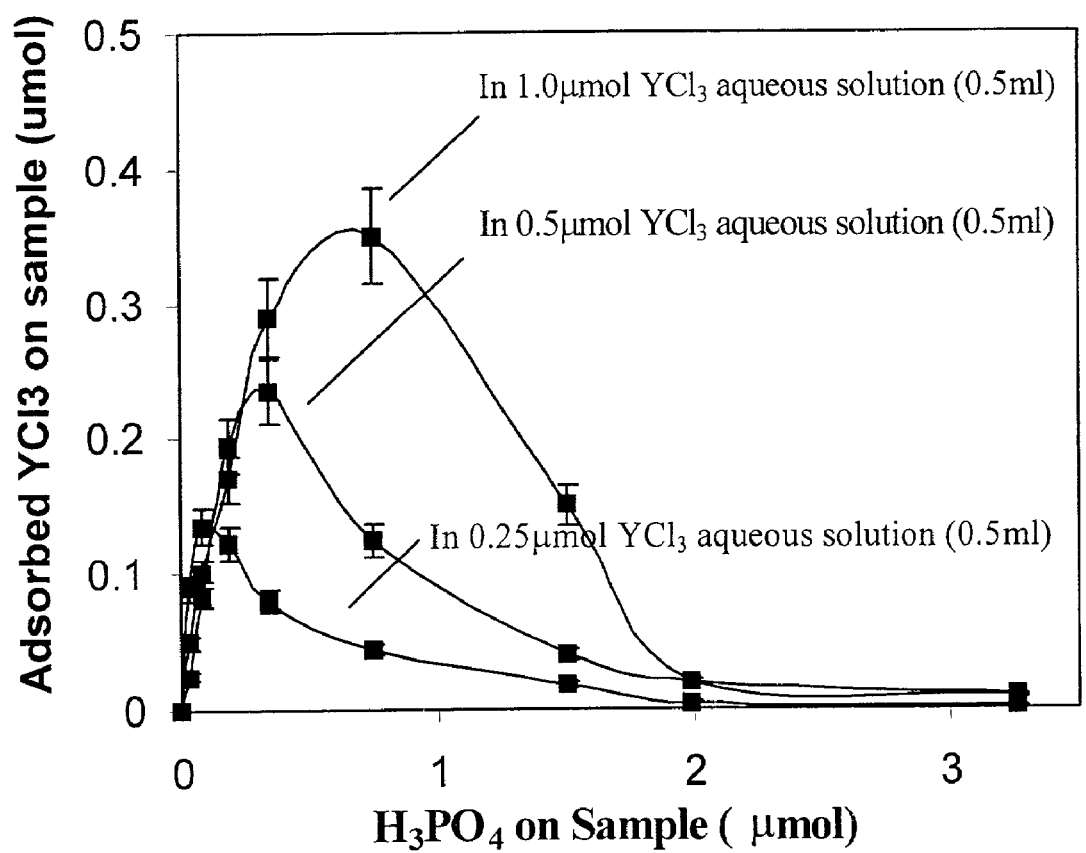
FIG. 21 shows effect of absorbed $H_3PO_4$ on deposited $YPO_4$ amount on sample surface.

The SEM photographs of surfaces coated with different polymer solutions were shown in FIG. 14. The samples coated with chloroform solutions (Tecoflex and Carbothane) have rougher surface than aqueous solution (AST-B and AST-B/Carbothane). Some $CaHPO_4$ particles on the surface could be observed even if they have been embedded by Tecoflex and Carbothane layers.

Figure 8:
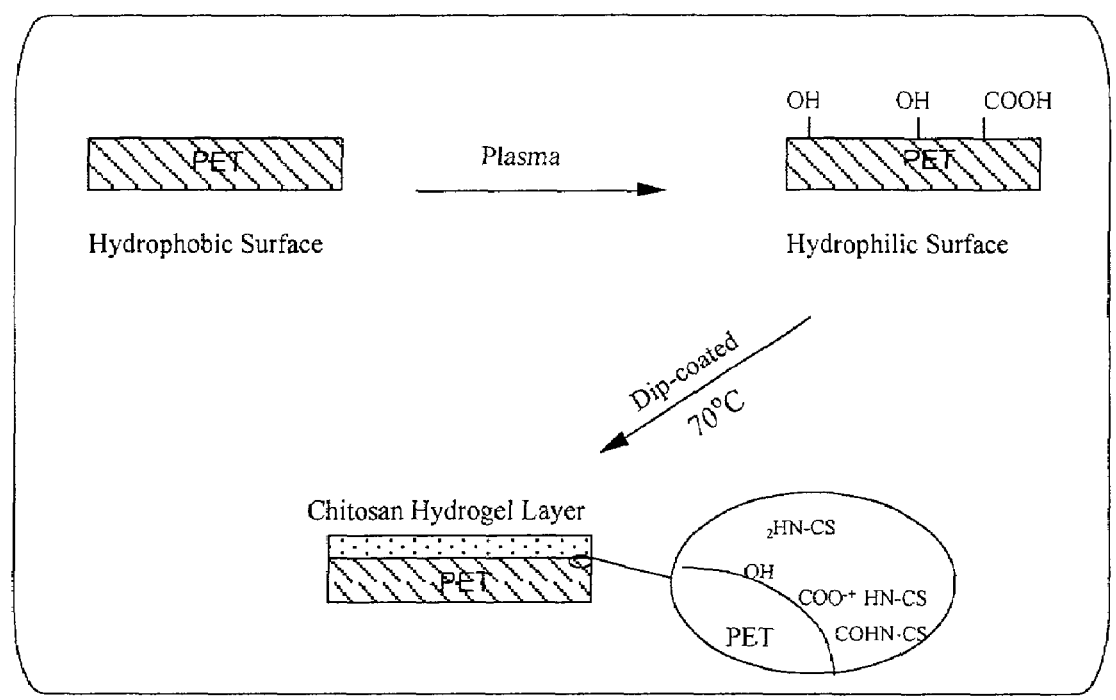
FIG. 8 shows surface modification of PET balloon by chitosan hydrogel.

In order to attach hydrophilic chitosan hydrogel to the hydrophobic PET surface, PET balloon surface was treated by oxygen plasma to create functional groups such as —OH and —COOH. Aqueous solutions of chitosan and lactic acid can form hydrogels after heating (16, 17) Chitosan is first dissolved in lactic acid solution to form chitosan lactate salt. By dip-coating and heating, the dehydration of chitosan lactate salt will occur to form amide groups, while the polycondensation of lactic acid occurs to form lactic acid side chains. The formation of chitosan hydrogel is due to the physical crosslinking through hydrophobic side chains aggregation and intermolecular interactions through hydrogen bonds between side and main chains, which eventually lead to a corresponding decrease of chitosan chain mobility in the aqueous solutions. (19, 20). As illustrated in FIG. 8, chitosan hydrogel attached to the PET surface due to the formation of the covalent bond, ionic bond and hydrogen bonds between the functional groups on the surface and —$NH_2$ groups of chitosan during the heating process. Polypropylene films have been coated with chitosan for improving dyeing behavior (21).

The chitosan hydrogel layer on the PET surface is smooth and transparent. It is pH-sensitive and swells extensively in aqueous phosphoric acid solution. The unreacted amino groups of chitosan are ionized by the phosphoric acid, and the acid attached to the gels by the ionic bonds (FIG. 9). The hydrogel layer on the surface could absorb as high as 15-fold water by weight. During the swelling process, the hydrogel layer attached on PET surface expands extensively in all directions and divided into many small pieces due to the internal intention as shown in FIG. 3A.

The influence of $H_3PO_4$ concentration on the adsorption efficiency could be divided into three periods. At concentrations higher than 5 mM solutions, the hydrogel layer adsorption was maximal at $1.8'10^{-3}$ mmol $H_3PO_4/cm^2$ at 25° C. and $2.5'10^{-1}$ mmol $H_3PO_4/cm^2$ at 50° C., which is independent to the concentration. The adsorption efficiency decreases with the increase of the concentration. In the solution concentration between 0.2 mM and 5 mM, the hydrogel layer adsorbed more at higher $H_3PO_4$ concentration, while the adsorption efficiency decrease with the increase of concentration.

The efficiency reaches the highest values (70%–80%) at 0.2 mM solution. Below this concentration, the adsorption efficiency decreases with the concentration. As indicated in FIG. 7, the adsorption process is always faster in higher $H_3PO_4$ concentration solutions.

Radiation dosimetry is critical in vascular brachytherapy. Overdose and underdose could result in reduction of the treatment effectiveness and may increase the radiation toxicity.

The radioisotope capacity of this system has been computed. The carrier-free activity of $^{32}P$ isotope used is 8500–9120 Ci/mmol, so the maximum achievable activity density is 20 Ci/cm$^2$ on the PET surface. The typical activity needed for the intracoronary radiation is about 2 mCi/cm$^2$ for a 2 cm treatment length. This calculation indicates that surface capacity is approximately 1000 fold greater than required.

The feasibility of providing uniform dosimetry is also critical in vascular brachytherapy. In usual wire-based delivery procedures, the source is not centered in available lumen. The lack of centering may be associated with overdosing on one side of the vessel wall and underdosing the other side. In this case, the use of radioactive balloon surface would provide the best attainable uniformity of dose at the arterial wall even the balloon or vessel takes a turn. Another configuration of the radioactive surface allowed by the high capacity for radioisotope would be as a flexible polymer wire coated with the radioisotope. The flexible wire offers the ability for repeat use.

The surface modification of nylon balloon after plasma treatment was also achieved by the method according to the invention and similar results have been obtained. Meanwhile, the chitosan hydrogel on the surface has the ability to chalet radioisotope ions like $^{188}Re$, which provides another alternative of a radioactive balloon surface.

After adsorbing $^{32}P$-phosphoric acid onto the PET balloon surface, the surface is then encapsulated with different polymer layers to prevent leakage of the isotope into the patient. Encapsulation is desirable even if a coated wire system is used and inserted into a closed catheter, in case of a leak developing in the catheter. The adsorbed phosphoric acid on the sample surface released readily in the aqueous solutions. Especially in the phosphate buffer, nearly 40% $H_3PO_4$ released into the buffer after first 1 hour incubation, since the ionic bonds are readily hydrolyzed in aqueous solutions.

In order to prevent leakage of isotope, the adsorbed phosphoric acid was precipitated on surface as calcium phosphate ($CaHPO_4$) by saturated $Ca(OH)_2$/5% $CaCl_2$ solution. $CaHPO_4$ is insoluble to some extent in neutral and basic aqueous solutions, and forms a complex with chitosan hydrogel. This convenient method for depositing calcium phosphate mineral on the surface of biomaterials has other potential biomedical applications such as dental and skeletal prosthesis (22, 23). The swellability of hydrogel decreased and the surface became rough with fine particles dispersed evenly on the surface as shown in SEM photograph (FIG. 12). The formation of insoluble calcium phosphate decreases the off-rate to 15% after 1 hour and 40% after 24 hours incubation.

Different polymer solutions were used to dip-coat the samples in our experiment. AST-A and AST-B with 3% crosslinker use water as solvent. These polymers with functional groups were crosslinked during the drying process, which gives a denser layer and better adhesion of coating to the hydrogel surface. However, a small amount of $CaHPO_4$ could be dissolved into aqueous solution and migrate to the surface of coatings. Especially, the isotope off-rate after 1 hour is about 1.2% for poly(styrene-acrylic acid) coated sample, since the $CaHPO_4$ was dissolved more in the acidic condition. On the contrary, $CaHPO_4$ could not be dissolved in chloroform during Tecoflex and Carbonate coating process. The main reason for the leakage of these coatings might be due to poor adhesion to the hydrogel surface. Combining these two methods, coating AST-B first and then covering again with Carbonate solution, gave the best results as shown in Table 2. The off-rate of $^{32}P$-isotope decreased dramatically to 0.01% after 1 hour, and to 0.1% after 24 hours incubation.

In practical intracoronary radiation, the balloons with isotope were inserted into body for only 30 minutes to irradiate the artery wall and the actually activity needed is about 2 mCi/cm$^2$. So the maximum dosage leaked into body is about 2 mCi/cm$^2$ according to the calculation. As a general rule, the polyurethane layers need to be of sufficient thickness to keep the level of isotope leakage to be tolerable (24). The thick coatings might affect the mechanic propriety of balloon, while the problem becomes minor when this method is applied to the wire system.

In summary, according to the invention, $^{32}P$ (o-phosphoric acid) was adsorbed by pH-sensitive chitosan hydrogel on PET balloon surface as a novel b-emitting delivery system for intracoronary radiation. The radiation dose of the balloons could be manipulated by changing the $^{32}P$ concentration in the solution and also the proportion of cold and hot phosphoric acid. To prevent leakage of $^{32}P$-isotope into the patient, absorbed phosphoric acid was precipitated as calcium phosphate, which formed fine white particles on the surface. Different hydrophobic polymer solutions were dip-coated to encapsulate isotope on the sample surface. The best results were obtained by coating with two different polyurethane solutions together, which dramatically reduced the off-rate of isotope to 0.01% after 1 hour incubation in PBS.

Although several embodiments have been shown and described, numerous variations and modifications may occur to those skilled in the art. The invention is not limited to the preferred embodiments illustrated and its scope is defined only by the appended claims.

TABLE 1

The details of polymer solutions

| Coating | Company | Name | Ingredients | Solvent |
|---|---|---|---|---|
| 1 | AST Products Inc. | AST-A | Poly(styrene-acrylic acid) And 3% crosslinker | Water |
| 2 | AST Products Inc. | AST-B | Polyurethane and 3% crosslinker | Water |
| 3 | Thermedics Inc. | Tecoflex | Polyether based aliphatic Polyurethane | Chloroform |
| 4 | Thermedics Inc. | Carbonthane | Polycarbonate based aliphatic polyurethane | Chloroform |

TABLE 2

The off-rate of $^{32}$P-phosphoric acid adsorbed surfaces with different treatments.

| Sample | Description | 1 hour off rate | 2 hour off rate | 3 hour off rate | 24 hour off rate |
|---|---|---|---|---|---|
| 1 | $^{32}$P isotope on surface | 40% | 60% | 75% | 90% |
| 2 | Then Ca(OH)$_2$ | 15% | 18% | 25% | 40% |
| 3 | AST-A coated | 1.2% | 1.8% | 2.5% | 3.0% |
| 4 | AST-B coated | 0.2% | 0.25% | 0.25% | 0.3% |
| 5 | Tecoflex coated | 0.3% | 0.5% | 0.6% | 2.0% |
| 6 | Carbothane coated | 0.3% | 0.4% | 0.5% | 2.2% |
| 7 | AST-B/Carbonate Coated | 0.01% | 0.02% | 0.04% | 0.1% |

REFERENCES

1. Gruentzig A R, King S B, Schlumpf M, et al. Long-term followup after percutaneous transluminal coronary angioplasty. N Engl J Med 1987; 316:1127–32
2. Nobuyoshi M. Kimura T. Nosaka H, et al. Restenosis after successful percutaneous transluminal coronary angioplasty: serial angiographic follow-up of 229 patients. J Am Coll Cardiol 1988; 12:616–23
3. Muller D W M, Ellis S G, Topol E J. Colehicine and antineoplastic therapy for prevention of restenosis after percutaneous coronary interventions. J Am Coll Cardiol 1991; 17:26B–31B
4. Urban P, Buller N, Fox K, et al. Lack of effect of warfarin on the restenosis rate or on clinical outcome after balloon coronary angioplasty. Br Heart J 1988; 60:485–8
5. Wiedermann J G, Marboe C, Amols H, Schwartz A, Weinberger J. Intracoronary irradiation markedly reduces restenosis after balloon angioplasty in a porcine model. JACC 1994; 23(6):1491–8
6. Wiedermann J G, Marboe C, Amols H, Schwartz A, Weinberger J. Intracoronary irradiation markedly reduces neointimal proliferation after balloon angioplasty in swine: persistent benefit at 6-month follow-up. JACC 1994; 25(6):1451–6
7. Mazur W, Ali M N, Khan M M, Dabaghi S F, DeFelice C A, Paradis J P, Butler E B A, Wright E, Fajardo L F B, French A and Raizner A E. High dose rate intracoronary radiation for inhibition of neointimal formation in the stented and balloon-injured porcine models of restenosis: Angiographic, morphometric, and histopathologic analysis. Int J Rad One Biol Phys 1996; 36(4):777–788
8. Waksman R, Robinson K A, Crocker I R, Gravanis M B, Cipolla G D, and King S R. Endovascular low-dose irradiation inhibits neointima formation after coronary artery balloon injury inswine: A possible role for radiation therapy in restenosis prevention. Circulation 1995; 91(5): 1533–9
9. Verin V, Popowski Y, Urban P, et al. Intra-arterial beta irradiation prevents neointimal hyperplasia in a hypercholesterolemic rabbit restenosis model. Circulation 1995; 92:2284–90
10. Condado J A, Waksman R, Gurdiel O, et al. Long-term angiographic and clinical outcome after percutaneous transluminal coronary angioplasty and intracoronary radiation therapy in humans. Circulation 1997; 96:727–32
11. Teirstein P S, Massullo V, Jani S, et al. Catheter-based radiotherapy to inhibit stenosis after coronary stenting. N Engl J Med 1997; 336:1697–703
12. Verin V, Urban P, Popowski Y, et al. Feasibility of intracoronary B-irradiation to reduce restenosis after balloon angioplasty, a clinical pilot study. Circulation 1997; 95:1138–44
13. Weinberger J. Intracoronary radiation using radioisotope solution-filled balloons. Herz 1998; 23:366–72
14. Muzzarelli R A A. Chitin. Pergamon, Oxford 1977
15. Guibal E. Dambies L, Milot C, Roussy J. Influence of polymer structural parameters and experimental conditions on metal anion sorption by chitosan. Polym Intern 1999:48(8):671–80
16. Nishimura Y, Kakuta I, Takeda H, et al. Effect of natural chelating agents on the intestinal-absorption of radiostrontium in rats. Radiation Protection Dosimetry 1994:53 (1–4):331–34
17. Park K B, Kim Y M, Kim J R. Radioactive chitosan complex for radiation therapy U.S. Pat. No. 5,762,903
18. Qu X, Weinberger J. Novel B-emitting poly(ethylene terephtalate) surface modification. J Biomed Material Research In press
19. Qu X, Wirsen A, Albertsson A C. Structural change and swelling mechanism of pH-sensitive hydrogels based on chitosan and D, L-lactic acid. J Appl Polym Sci 1999; 74(13):3186–92
20. Qu X, Wirsen A, Albertsson A C. Synthesis and characterization of pH-sensitive hydrogels based on chitosan and D,L-lactic acid. J Appl Polym Sci 1997; 74(13): 3193–02
21. Rochery M, Lam T M, Crighton J S. FTIR&ATR analyses on a polypropylene(PP) surface after plasma treatment in the study of chitosan surface grafting to improve PP dyeing behavior. Macromol symp 1997; 119:277–82
22. Pioletti D P, Takei H. Lin T, et al. The effect of calcium phosphate cement particles on osteoblast functions. Biomaterials 2000:21:1103–14
23. Varma H K, Yokogawa Y, Espinosa F F, et al. Porous calcium phosphate coating over phosphorylated chitosan film by a biomimetic method. Biomaterials 1999:20: 879–84
24. Lewis R E, Tercho G P, Walsh P R. Intra-coronary radiation devices containing Ce-144 or Ru-106. PCT Publication No. WO 99/17812
25. Roberts G A F, Chitin Chemistry, Macmillan, Houndmills 1992
26. Zamora P O, Osakis, Som P, Ferretti J A, Choi J S, Hu C, Tsang R, Kuan H M, Singletary S, Stern R A, Oster Z H, Radiolabeling Brachytherapy Sources with Re-188 through Chelating Microfilms: Stents, Journal of Biomedical Materials Research, Vol 53, No. 4 pp 244–251 (May 11, 2000)

We claim:

1. A method of making a radioactive source, comprising:
   forming a polymer layer on a substrate material, the formation being substantially free of inorganic polymers, and;
   exposing the polymer layer to a radioactive isotope so that the radioactive isotope is adsorbed in the layer.
2. The method according to claim 1, further comprising the step of providing a substrate material.
3. The method according to claim 2, wherein the step of providing a substrate material comprises providing a polymer substrate material.
4. The method according to claim 3, wherein the step of providing a polymer substrate material comprises providing a substrate material of polyethylene terephtalate.

5. The method according to claim 2, wherein the substrate material is in the form of an inflatable balloon.

6. The method according to claim 2, wherein the substrate material is in the form of a wire.

7. The method according to claim 1, wherein the step of forming a layer of polymer comprises forming a layer of hydrogel.

8. The method according to claim 2, further comprising the step of treating the substrate material oxygen plasma to obtain a hydrophilic surface, before the step of forming a polymer layer.

9. The method according to claim 1, wherein the step of exposing comprises exposing the polymer layer to a $^{32}P$ radioisotope.

10. The method according to claim 9, wherein the step of exposing comprises exposing the polymer to phosphoric acid.

11. The method according to claim 1, wherein the step of exposing comprises exposing the polymer layer to a $^{90}Y$ radioisotope.

12. The method according to claim 11, wherein the step of exposing comprises exposing the polymer to a solution of $YCl_3$.

13. The method according to claim 1, wherein the step of exposing comprises exposing the polymer layer to a $^{144}Ce$ radioisotope.

14. The method according to claim 13, wherein the step of exposing comprises exposing the polymer to a solution of $CeCl_3$.

15. The method according to claim 1, wherein the step of exposing comprises exposing the polymer layer to a $^{188}Re$ radioisotope.

16. The method according to claim 1, further comprising the step of coating the exposed layer with a sealant.

17. The method according to claim 16, wherein the step of coating comprises coating the exposed layer with a polymer sealant.

18. The method according to claim 16 wherein the step of coating comprises coating the exposed layer with poly(stylene-acrylic acid).

19. The method according to claim 16, wherein the step of coating comprises coating the exposed layer with a poly urethane solution.

20. The method according to claim 16, wherein the step of coating comprises coating the exposed layer with a polyether based aliphatic polyurethane resin.

21. The method according to claim 16, wherein the step of coating comprises coating the exposed layer with an AST-B (poly(stylene-polyurethane)) solution and then coating with a polycarbonate based aliphatic polyurethane solution.

22. A method for making a radioactive source comprising:
    forming an organic polymer layer on a substrate material; and
    exposing the substrate material to a radioactive isotope so that the radioactive isotope is absorbed in the layer.

23. The method according to claim 22, further comprising the step of providing a substrate material of polymer.

24. The method according to claim 22, further comprising the step of coating the exposed layer to seal the radioactive isotope.

25. A method for making a radioactive source comprising:
    providing a substrate material;
    forming a layer of organic polymer material on the substrate material;
    exposing the polymer layer to a radioactive isotope material so that the radioactive isotope is adsorbed in the layer; and
    coating the exposed layer to seal the radioactive isotope material.

26. A method for making a radioactive source for treating a patient, comprising:
    providing a polymer substrate material;
    forming a polymer layer of organic on the substrate material; and exposing the substrate material to a radioactive isotope so that the radioactive isotope is absorbed in the layer.

27. A product made according to the method of claim 1.

28. A product made according to the method of claim 22.

29. A product made according to the method of claim 25.

30. A product made according to the method of claim 26.

* * * * *